US010625265B2

(12) United States Patent
Hoffmann, Jr. et al.

(10) Patent No.: US 10,625,265 B2
(45) Date of Patent: Apr. 21, 2020

(54) OPTICAL TEST PLATFORM

(71) Applicant: bioMerieux, Inc., Durham, NC (US)

(72) Inventors: Jack R. Hoffmann, Jr., St. Louis, MO (US); Gregory R. Maes, Fenton, MO (US); Jeffrey Edward Price, Wildwood, MO (US); Jared Ian Bullock, St. Louis, MO (US); Samuel B. Crandall, Troy, MO (US); Jacky S. Yam, St. Louis, MO (US); Christopher George Kocher, St. Louis, MO (US); Walter J. Clynes, O'Fallon, MO (US)

(73) Assignee: BIOMERIEUX, INC., Durham, NC (US)

( * ) Notice: Subject to any disclaimer, the term of this patent is extended or adjusted under 35 U.S.C. 154(b) by 2 days.

(21) Appl. No.: 15/958,771

(22) Filed: Apr. 20, 2018

(65) Prior Publication Data
US 2018/0306701 A1 Oct. 25, 2018

Related U.S. Application Data

(60) Provisional application No. 62/487,807, filed on Apr. 20, 2017, provisional application No. 62/487,796, (Continued)

(51) Int. Cl.
B01L 3/00 (2006.01)
G01N 21/01 (2006.01)
(Continued)

(52) U.S. Cl.
CPC ............ B01L 3/50853 (2013.01); G01N 1/10 (2013.01); G01N 15/06 (2013.01); G01N 21/01 (2013.01);
(Continued)

(58) Field of Classification Search
CPC ......... B01L 3/50853; B01L 2300/0654; B01L 2300/0803; B01L 2200/14; B01L 2300/12;
(Continued)

(56) References Cited

U.S. PATENT DOCUMENTS 2,157,438 A 5/1939 Sparks
2,436,262 A 2/1948 Miller
(Continued)

FOREIGN PATENT DOCUMENTS

CN 3159492 1/2000
CN 3383938 11/2003
(Continued)

OTHER PUBLICATIONS

International Search Report and Written Opinion for Application No. PCT/US2018/028699 dated Jul. 16, 2018, 14 pages.
(Continued)

Primary Examiner — Hina F Ayub
(74) Attorney, Agent, or Firm — Alston & Bird LLP

(57) ABSTRACT

Provided herein are an optical test platform and corresponding method of manufacturing the same. The test platform may include a shell defining a cavity for receiving a sample tube, a first aperture, and a second aperture. The first aperture and the second aperture of the shell may each be configured to optically couple the cavity with an exterior of the shell. The test platform may further include a first window and a second window embedded in the shell. The first window may seal a first aperture and the second window may seal a second aperture. The first window and second window may each permit the optical coupling of the cavity with the exterior of the shell. The first window and the second window may be optically coupled via the cavity, and
(Continued)

the shell may prohibit optical coupling between the first window and the second window through the shell.

27 Claims, 26 Drawing Sheets

Related U.S. Application Data filed on Apr. 20, 2017, provisional application No. 62/488,450, filed on Apr. 21, 2017, provisional application No. 62/487,860, filed on Apr. 20, 2017, provisional application No. 62/487,736, filed on Apr. 20, 2017.

(51) Int. Cl.
| | |
|---|---|
| *G01N 21/59* | (2006.01) |
| *G01N 21/47* | (2006.01) |
| *G01N 1/10* | (2006.01) |
| *G01N 21/27* | (2006.01) |
| *G01N 33/487* | (2006.01) |
| *G01N 21/03* | (2006.01) |
| *G01N 15/06* | (2006.01) |
| *G01N 21/51* | (2006.01) |
| *G01N 21/88* | (2006.01) |
| *G01N 21/93* | (2006.01) |

(52) U.S. Cl.
CPC ....... *G01N 21/0303* (2013.01); *G01N 21/274* (2013.01); *G01N 21/4738* (2013.01); *G01N 21/4785* (2013.01); *G01N 21/51* (2013.01); *G01N 21/5907* (2013.01); *G01N 21/8806* (2013.01); *G01N 21/93* (2013.01); *G01N 33/487* (2013.01); *G01N 33/48735* (2013.01); *B01L 2200/14* (2013.01); *B01L 2300/0654* (2013.01); *B01L 2300/0803* (2013.01); *B01L 2300/12* (2013.01); *G01N 21/474* (2013.01); *G01N 2015/0693* (2013.01); *G01N 2021/0168* (2013.01); *G01N 2021/0389* (2013.01); *G01N 2021/4769* (2013.01); *G01N 2021/598* (2013.01); *G01N 2201/126* (2013.01); *G01N 2201/12707* (2013.01)

(58) Field of Classification Search
CPC ......... G01N 33/48735; G01N 21/8806; G01N 15/06; G01N 21/0303; G01N 21/93; G01N 21/51; G01N 21/4785; G01N 21/4738; G01N 21/274; G01N 1/10; G01N 33/487; G01N 21/01; G01N 21/5907; G01N 21/474; G01N 2021/0168; G01N 2021/4769; G01N 2021/0389; G01N 2015/0693; G01N 2201/126; G01N 2201/12707; G01N 2021/598

See application file for complete search history.

(56) References Cited

U.S. PATENT DOCUMENTS

| | | | |
|---|---|---|---|
| 2,863,354 A | 12/1958 | Diehl et al. | |
| 2,874,606 A | 2/1959 | Leiterer | |
| 3,554,648 A | 1/1971 | Boostrom et al. | |
| 3,712,144 A | 1/1973 | Kuzel et al. | |
| 3,714,445 A | 1/1973 | Blachere et al. | |
| 3,775,013 A | 11/1973 | Simms | |
| 3,783,635 A | 1/1974 | Perez | |
| 3,809,912 A | 5/1974 | Henning | |
| 3,826,574 A | 7/1974 | Brown, Jr. | |
| 3,962,041 A | 6/1976 | Muller et al. | |
| 3,977,794 A | 8/1976 | Liedholz | |
| 4,118,625 A | 10/1978 | Underwood | |
| 4,193,692 A | 3/1980 | Wynn | |
| 4,291,983 A | 9/1981 | Kraft et al. | |
| 4,343,552 A * | 8/1982 | Blades ............ | G01N 21/53 |
| | | | 250/574 |
| 5,137,693 A | 8/1992 | Mawhirt | |
| 5,140,168 A | 8/1992 | King | |
| 5,331,177 A | 7/1994 | Kunisiak et al. | |
| 5,506,679 A | 4/1996 | Cooper et al. | |
| 5,604,590 A | 2/1997 | Cooper et al. | |
| 5,651,941 A | 7/1997 | Stark et al. | |
| 5,687,849 A | 11/1997 | Borenstein et al. | |
| 5,863,754 A | 1/1999 | Bajard | |
| 5,872,361 A | 2/1999 | Paoli et al. | |
| D439,673 S | 3/2001 | Brophy et al. | |
| 6,274,092 B1 | 8/2001 | Itoh | |
| D453,573 S | 2/2002 | Lafond et al. | |
| 6,359,689 B1 | 3/2002 | Stansell et al. | |
| 6,537,772 B1 | 3/2003 | Alarcon et al. | |
| 7,485,264 B2 | 2/2009 | Itoh | |
| D624,194 S | 9/2010 | Pack et al. | |
| 7,910,067 B2 | 3/2011 | Knight et al. | |
| 8,147,777 B2 | 4/2012 | Schacher et al. | |
| D679,412 S | 4/2013 | Khamu | |
| D687,567 S | 8/2013 | Jungheim et al. | |
| D709,625 S | 7/2014 | Baum et al. | |
| 2003/0005928 A1 | 1/2003 | Appel et al. | |
| 2003/0058450 A1 | 3/2003 | Mosley et al. | |
| 2005/0106746 A1 | 5/2005 | Shinn et al. | |
| 2006/0001865 A1 | 1/2006 | Bellalou et al. | |
| 2007/0269853 A1 | 11/2007 | Galiano | |
| 2008/0072664 A1 | 3/2008 | Hansen et al. | |
| 2010/0028859 A1 | 2/2010 | Moshe et al. | |
| 2010/0110220 A1 | 5/2010 | Leugers et al. | |
| 2011/0151503 A1 | 6/2011 | Galiano | |
| 2011/0306032 A1 | 12/2011 | Galiano et al. | |
| 2011/0306087 A1 | 12/2011 | Galiano et al. | |
| 2011/0307183 A1 | 12/2011 | Galiano et al. | |
| 2012/0009558 A1 | 1/2012 | Armstrong et al. | |
| 2012/0063956 A1 | 3/2012 | Truex et al. | |
| 2013/0022962 A1 | 1/2013 | Galiano | |
| 2013/0258336 A1 | 10/2013 | Ostermeyer et al. | |
| 2015/0086971 A1 | 4/2015 | Branch et al. | |
| 2015/0108076 A1 | 4/2015 | Branch et al. | |
| 2016/0160260 A1 | 6/2016 | Marshall et al. | |

FOREIGN PATENT DOCUMENTS

| | | |
|---|---|---|
| CN | 2919238 | 7/2007 |
| CN | 300905477 | 12/2007 |
| CN | 201141824 | 10/2008 |
| CN | 301068253 | 11/2008 |
| CN | 204142554 | 2/2010 |
| CN | 203479704 | 3/2014 |
| CN | 302968146 S | 6/2014 |
| CN | 302983583 S | 6/2014 |
| CN | 302995249 S | 6/2014 |
| CN | 103923827 | 7/2014 |
| CN | 303227067 S | 12/2014 |
| CN | 104266895 | 1/2015 |
| DE | 3516529 | 11/1986 |
| DE | 3608552 A1 | 9/1987 |
| DE | 202004020585 | 9/2005 |
| EP | 3023768 | 5/2016 |
| GB | 150 183 A | 9/1920 |
| GB | 4028381 | 1/2013 |
| GB | 4028382 | 1/2013 |
| JP | 3049676 | 6/1998 |
| JP | H10 284848 A | 10/1998 |
| JP | 3061144 | 9/1999 |
| JP | 2003/000224 | 1/2003 |
| KR | 100580312 | 5/2006 |
| KR | 20090081998 | 7/2009 |
| KR | 20090082060 | 7/2009 |
| KR | 100580313 | 5/2018 |
| WO | WO 1993/009440 A1 | 5/1993 |
| WO | WO 1995/25950 A1 | 9/1995 |
| WO | WO 1998/000701 A1 | 1/1998 |

(56) References Cited

FOREIGN PATENT DOCUMENTS

| WO | WO 1998/047999 A1 | 10/1998 |
| WO | WO 2000/065332 A1 | 11/2000 |
| WO | WO 2001/063253 A1 | 8/2001 |
| WO | WO 2004/015136 A1 | 2/2004 |
| WO | WO 2008/039442 A1 | 4/2008 |
| WO | WO 2010/090391 A2 | 8/2010 |
| WO | WO 2010/097687 A1 | 9/2010 |
| WO | WO 2010/108804 A1 | 9/2010 |
| WO | WO 2014/137333 A1 | 9/2014 |
| WO | WO 2015/026794 A1 | 2/2015 |
| WO | WO 2015/164274 A1 | 10/2015 |
| WO | WO 2016/049604 A1 | 3/2016 |
| WO | WO 2016/051267 A1 | 4/2016 |
| WO | WO 2016/191646 A1 | 12/2016 |

OTHER PUBLICATIONS

International Search Report and Written Opinion for Application No. PCT/US2018/028696 dated Sep. 7, 2018.
International Search Report and Written Opinion for Application No. PCT/US2018/028701 dated Sep. 10, 2018.
International Search Report and Written Opinion for Application No. PCT/US2018/028702 dated Sep. 10, 2018.

* cited by examiner

OPTICAL TEST PLATFORM

CROSS-REFERENCE TO RELATED APPLICATIONS

This application claims the benefit of each of the following: U.S. Provisional Application No. 62/487,807, which is entitled "Optical Test Platform" and was filed Apr. 20, 2017; U.S. Provisional Application No. 62/487,796, which is entitled "Optical Density Instrument And Systems And Methods Using The Same" and was filed Apr. 20, 2017; U.S. Provisional Application No. 62/488,450, which is entitled "Optical Density Instrument And Systems And Methods Using The Same" and was filed Apr. 21, 2017; U.S. Provisional Application No. 62/487,860, which is entitled "Tip Resistant Optical Testing Instrument" and was filed Apr. 20, 2017; and U.S. Provisional Application No. 62/487,736, which is entitled "Method, Apparatus, And Computer Program Product For Controlling Components Of A Detection Device" and was filed Apr. 20, 2017. Each of the foregoing applications is hereby incorporated by reference in its entirety.

BACKGROUND

In microbiology laboratories and other similar settings, lab technicians, scientists, and other practitioners use laboratory equipment to measure conditions of liquid suspensions. The suspensions may be observed and manipulated in clear polystyrene test tubes, glass test tubes, or other similar vials. The practitioner may utilize various devices or instruments to perform readings and measurements on the liquid in a tube. The practitioner may also manipulate the fluid while performing measurements, or intermittingly between measurements. In some examples, a practitioner may manipulate the fluid while monitoring a measurement or reading performed by an instrument.

One example of such a measurement performed in a microbiology lab includes measuring the turbidity and/or concentration of microorganisms in the liquid using an optical density instrument. The practitioner may use the instrument to achieve the optimal dilution of the sample by diluting the solutions with saline, or increasing the levels of microorganisms in the fluid. The optical density sensors in a device or instrument may be configured to detect light emitted in the area of the tube to measure characteristics of the liquid.

Existing instruments are often incapable of being used continuously during preparation of a sample because of poor visibility, interference from external and internal light sources, leaks and other electrical damage to the instrument's internal components, and high manufacturing costs. The inventors have identified numerous other deficiencies with existing technologies in the field, the remedies for which are the subject of the embodiments described herein.

BRIEF SUMMARY

Provided herein are an optical test platform and associated systems and methods. In some embodiments, the test platform may reduce interference at one or more sensors by reducing crosstalk and eliminating alternative light paths other than the intended paths through a sample.

A test platform according to embodiments of the present disclosure may be provided for facilitating the optical interrogation of a test sample. The test platform may include a shell defining a cavity for receiving a sample tube, a first aperture, and a second aperture. In some embodiments, the first aperture and the second aperture each may be configured to optically couple the cavity with an exterior of the shell. The test platform may include a first window embedded in the shell across the first aperture. The first window may seal the first aperture. The test platform may further include a second window embedded in the shell across the second aperture. The second window may seal the second aperture. The first window and second window each may be configured to permit the optical coupling of the cavity with the exterior of the shell. The first window and the second window may be optically coupled via the cavity, and the shell may be configured to prohibit optical coupling between the first window and the second window through the shell.

In some embodiments, the shell may be opaque, and in some further embodiments, the shell may be black.

The test platform may include a first mount for a first optical component and a second mount for a second optical component. The first mount may be optically coupled with the first aperture at the exterior of the shell, and the second mount may be optically coupled with the second aperture at the exterior of the shell. The first mount may be configured to position the first optical component to emit light into the cavity through the first window along a first axis, and the second mount may be configured to position the second optical component to receive light from the cavity through the second window along a second axis. In some embodiments, the first axis and the second axis are collinear, and in some other embodiments, the first axis and the second axis are not collinear. In some further embodiments, the first axis and the second axis may be perpendicular.

In some embodiments, the shell may further include a third aperture, and the test platform may further include a third window embedded in the shell. The third aperture may be configured to optically couple the cavity with the exterior of the shell, and the third window may seal the third aperture. In some embodiments, the first window, the second window, and the third window may be optically coupled via the cavity. The shell may be configured to prohibit optical coupling between the first window, the second window, and the third window through the shell. The third window may be offset from the first window and the second window, such that the third window may be configured to receive a portion of light emitted through the first window along an axis between the first window and the second window that is reflected within the cavity. In some embodiments, the first window and the second window each may be arranged on an axis that intersects a central axis of the cavity. The third window may be arranged on a second axis that is perpendicular to the axis of the first and second windows.

In some embodiments, at least one of the first window and the second window may be molded into the shell of the test platform.

The test platform may further include a first mount positioned adjacent the first aperture on an exterior of the shell. The first mount may be configured to receive a first optical component. In some embodiments, the first mount may include a first bore optically coupled with the first aperture and at least one attachment point, and the first mount may be configured to allow the first optical component to attach to the attachment point and optically communicate with the cavity via the first bore and the first aperture. In some embodiments, the first bore, the first aperture, and a first surface of the first window are oriented coaxially along an axis extending through a central axis of the cavity, and the first mount may be configured to aim the first optical component towards the central axis along the axis.

In some embodiments, the test platform may further include a second mount positioned adjacent the second aperture on an exterior of the shell, and the second mount may be configured to receive a second optical component. In some embodiments, the first mount may be configured to receive an emitter, and the second mount may be configured to receive a sensor.

The shell may further define a second cavity configured to receive a second sample tube.

In some embodiments, the test platform may include a spring defining a first leg and a second leg. The spring may be configured to elastically deform to cause the first leg and the second leg to each apply a force to a sample tube in a direction towards a point between the first leg and the second leg. In some embodiment, at least one of the first leg and the second leg may include rollers disposed thereabout, configured to rotate about the respective leg to allow the sample tube to be inserted. In some embodiments, the shell may include one or more stops and posts that retain the spring during, before, and/or after operation.

In another example embodiment, a method of manufacturing a test platform is provided. The test platform may include a shell defining a cavity for receiving a sample tube, a first aperture, and a second aperture. The first aperture and the second aperture each may be configured to optically couple the cavity with an exterior of the shell. The test platform may further include a first window embedded in the shell. The first window may seal the first aperture. The test platform may include a second window embedded in the shell. The second window may seal the second aperture. The first window and second window each may be configured to permit the optical coupling of the cavity with the exterior of the shell. The first window and the second window may be optically coupled via the cavity, and the shell may be configured to prohibit optical coupling between the first window and the second window through the shell. The method may include embedding the first window and the second window in the shell.

In some embodiments, embedding the first window and the second window in the shell may include positioning the first window and the second window in a shell mold, and molding the shell around the first window and the second window, such that the first window and the second window are embedded in the shell. The step of molding the shell around the first window and the second window may include molding an opaque material around the first window and the second window.

In some embodiments, molding the shell around the first window and the second window may include permanently affixing the first window and the second window to the shell without adhesives or fasteners.

In some further embodiments, molding the shell may include molding a first mount for a first optical component and a second mount for a second optical component. The first mount may be optically coupled with the first aperture at the exterior of the shell. The second mount may be optically coupled with the second aperture at the exterior of the shell. The first mount may be configured to position the first optical component to emit light into the cavity through the first window along a first axis, and the second mount may be configured to position the second optical component to receive light from the cavity through the second window along a second axis. In some embodiments, the first axis and the second axis may be collinear. In some other embodiments, the first axis and the second axis may not be collinear. In some further embodiments, the first axis and the second axis may be perpendicular.

BRIEF DESCRIPTION OF THE SEVERAL VIEWS OF THE DRAWINGS

Figure 1:
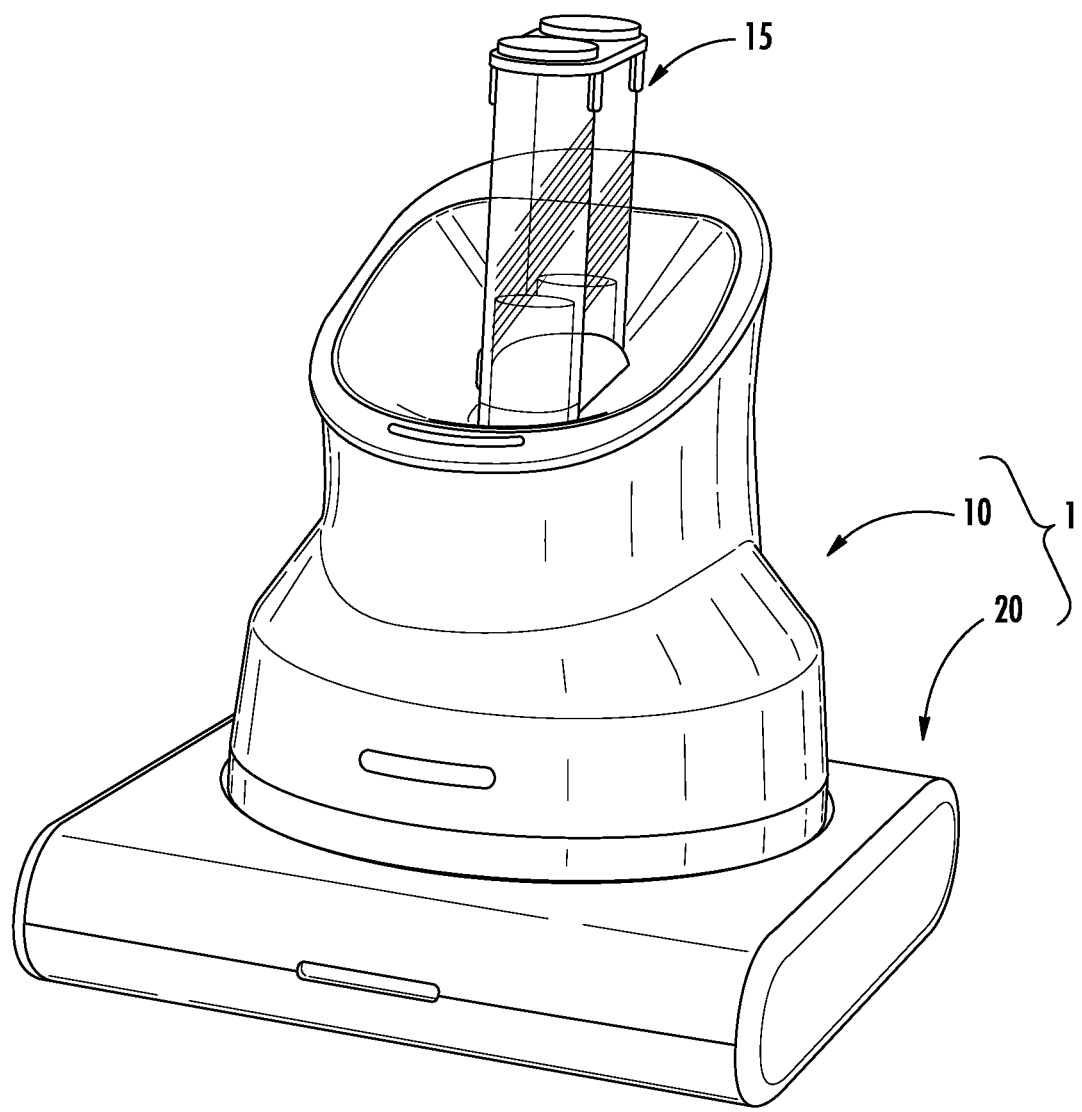
Figure 2:
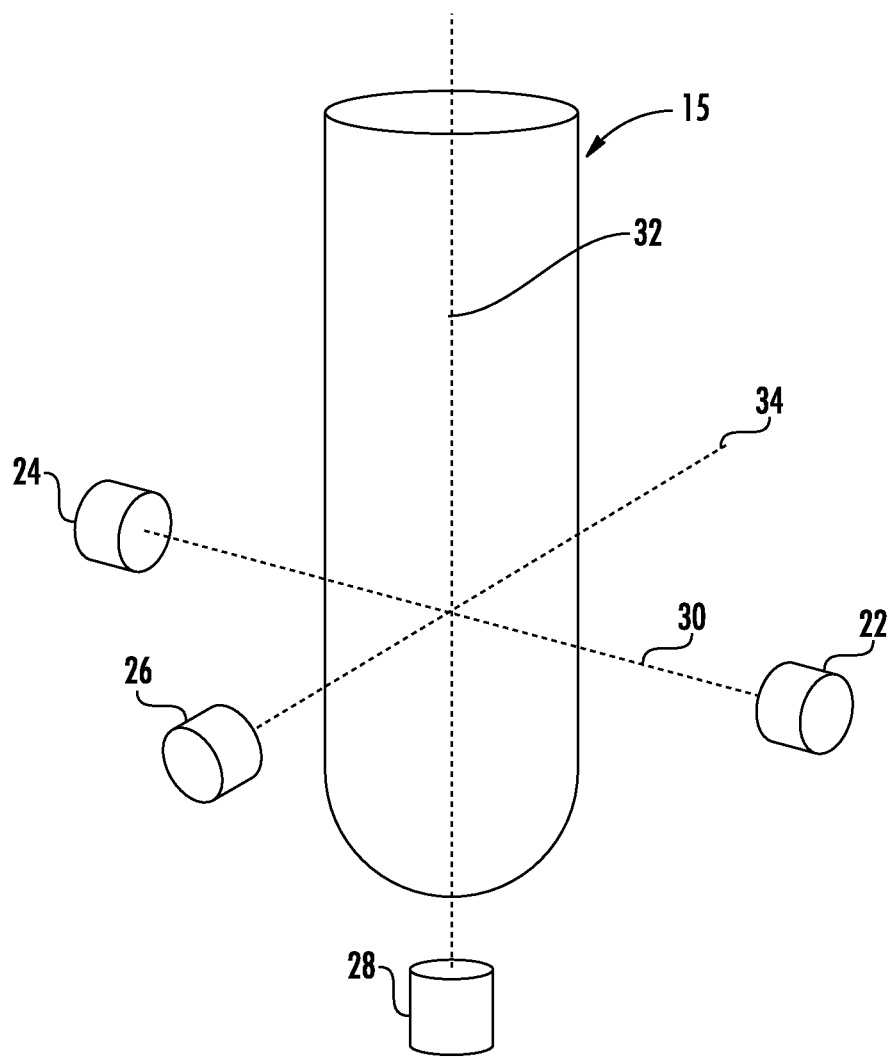
Figure 3:
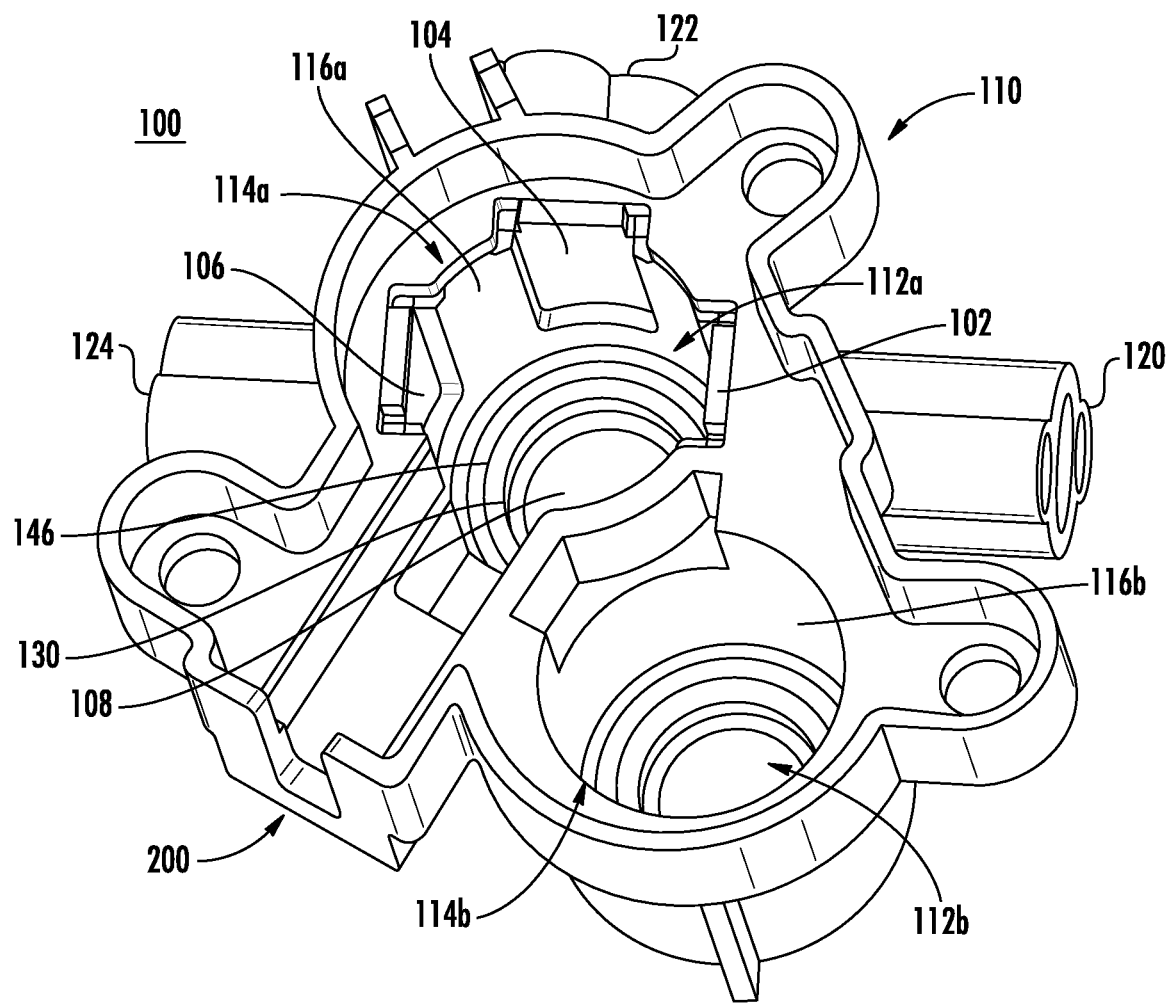
Figure 4:
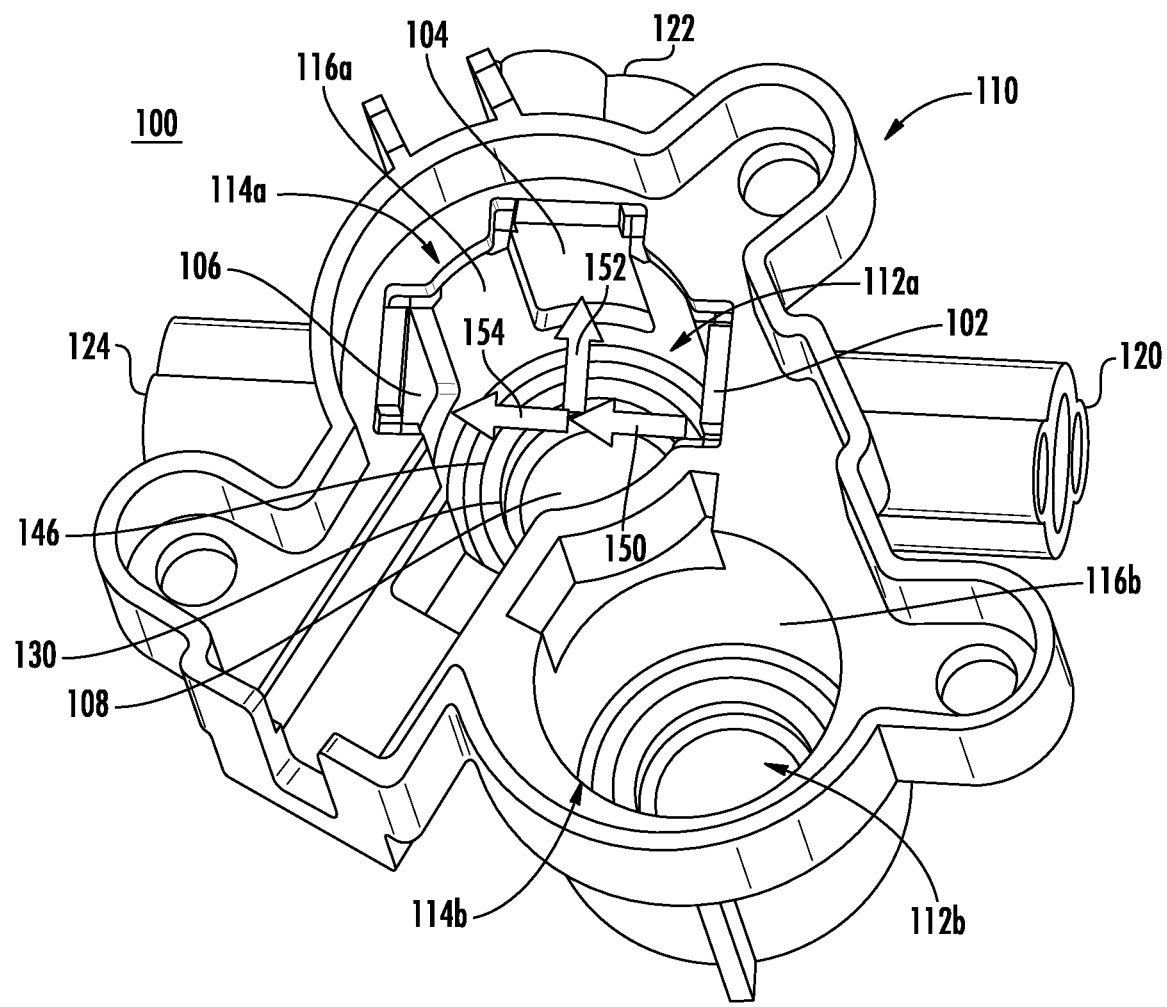
Figure 5:
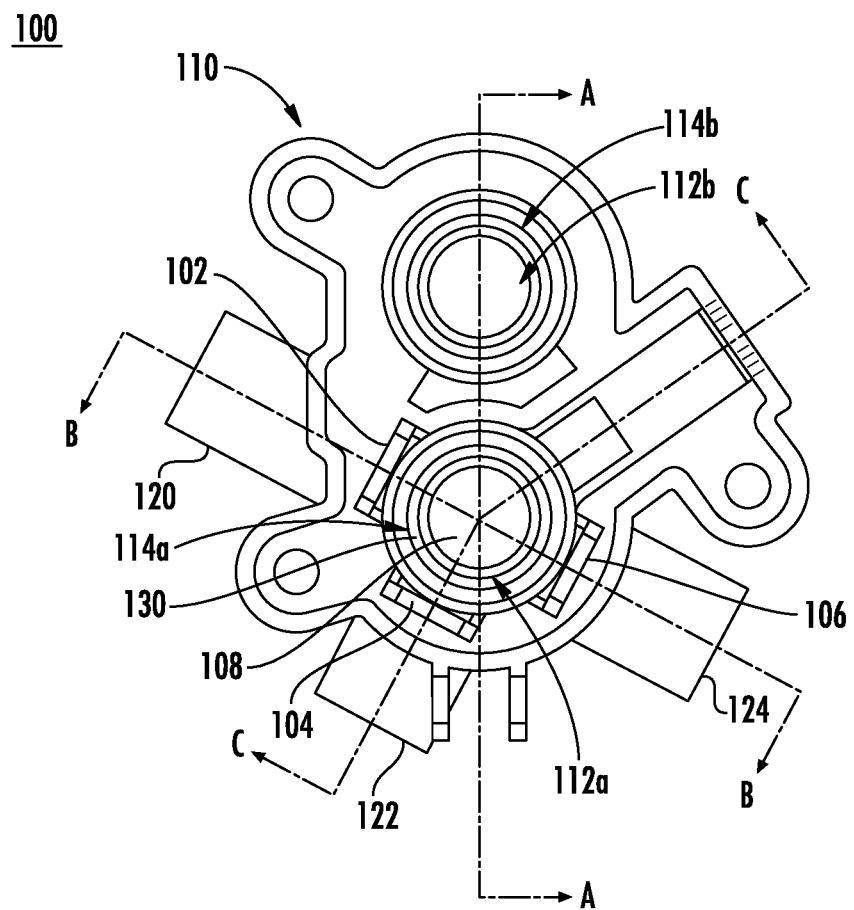
Figure 6:
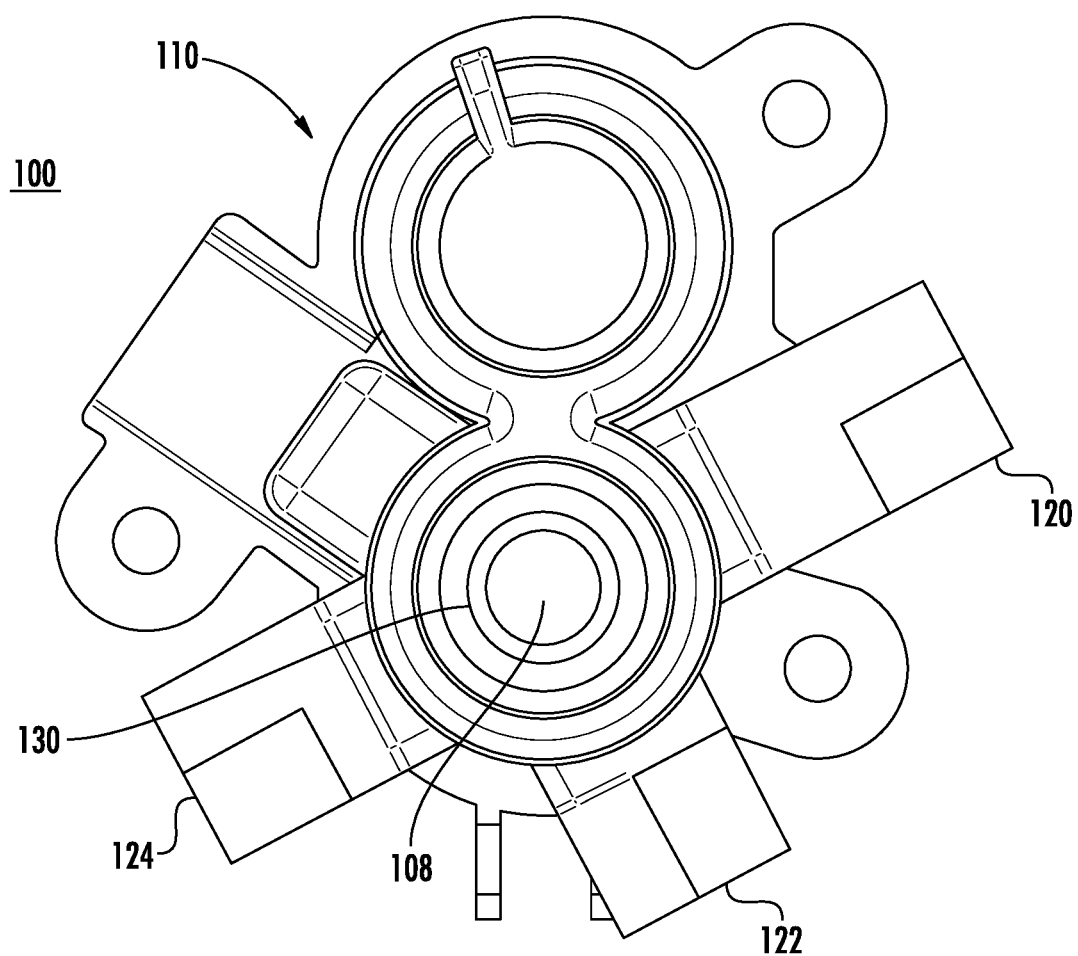
Figure 7:
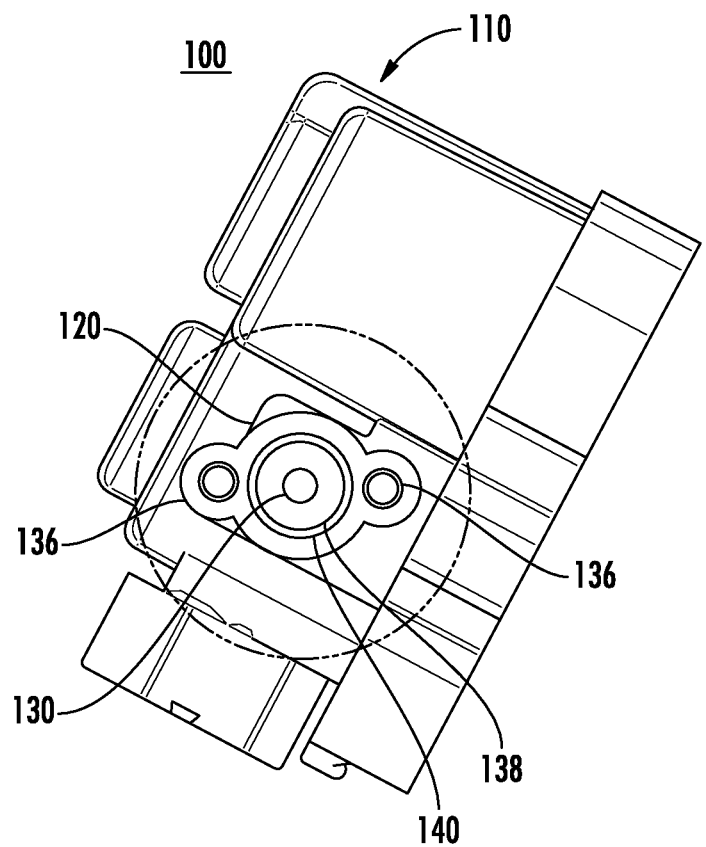
Figure 7A:
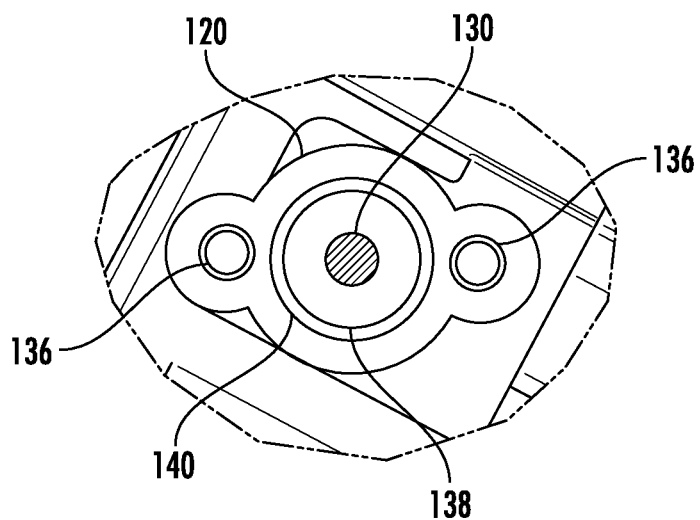
Figure 8:
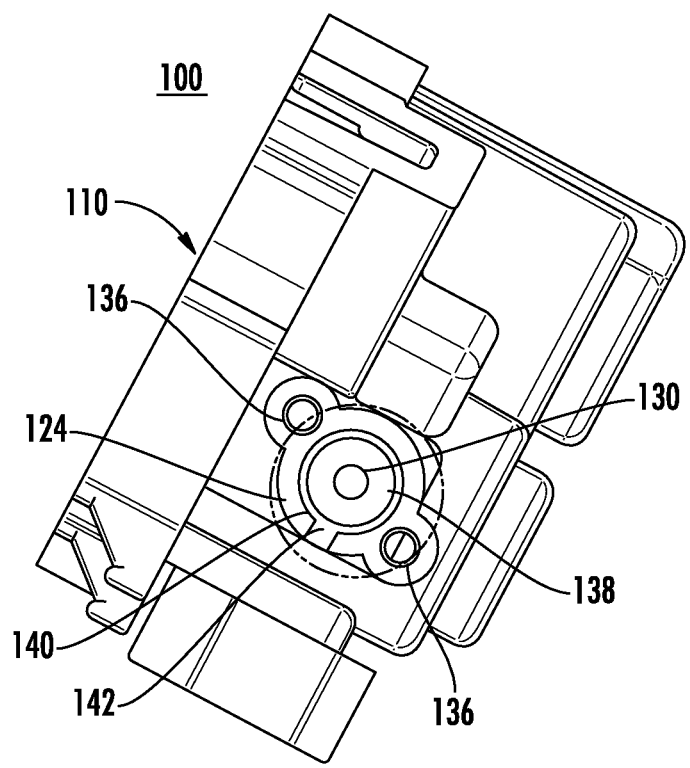
Figure 8A:
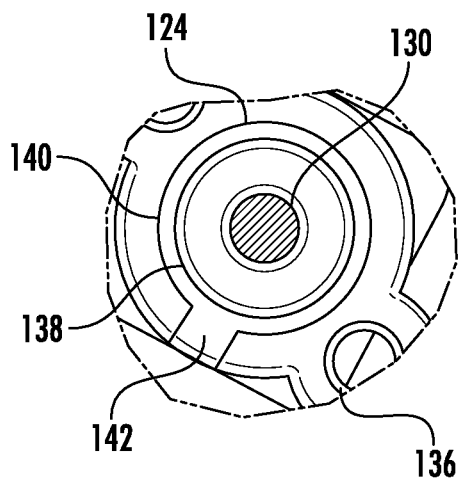
Figure 9:
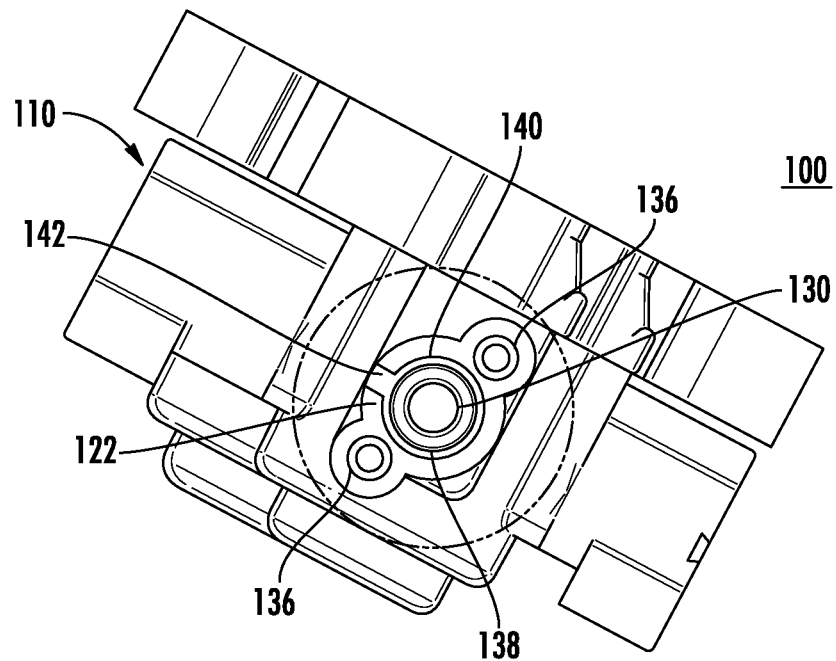
Figure 9A:
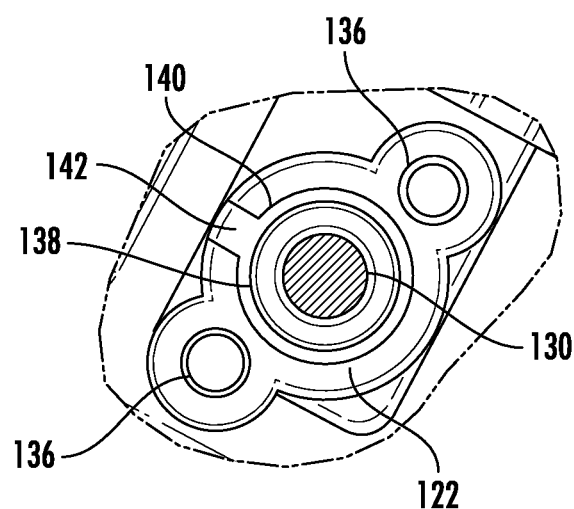
Figure 10:
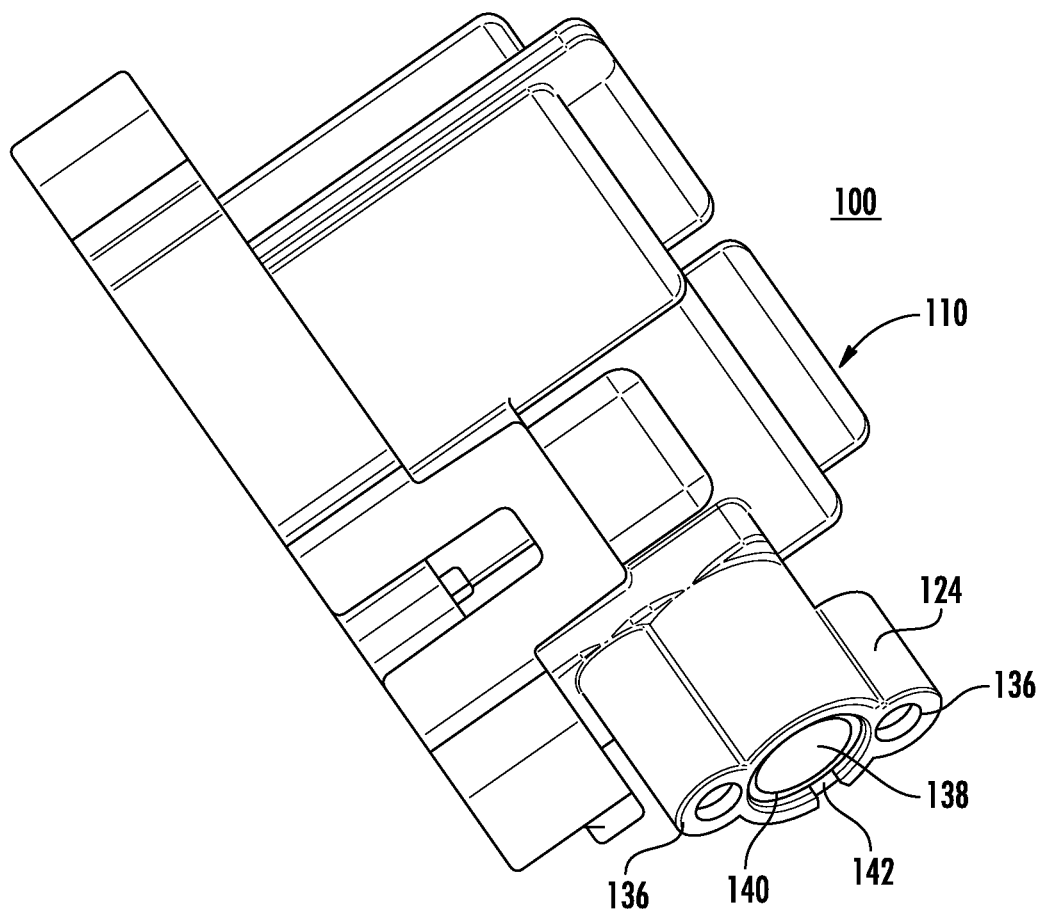
Figure 11:
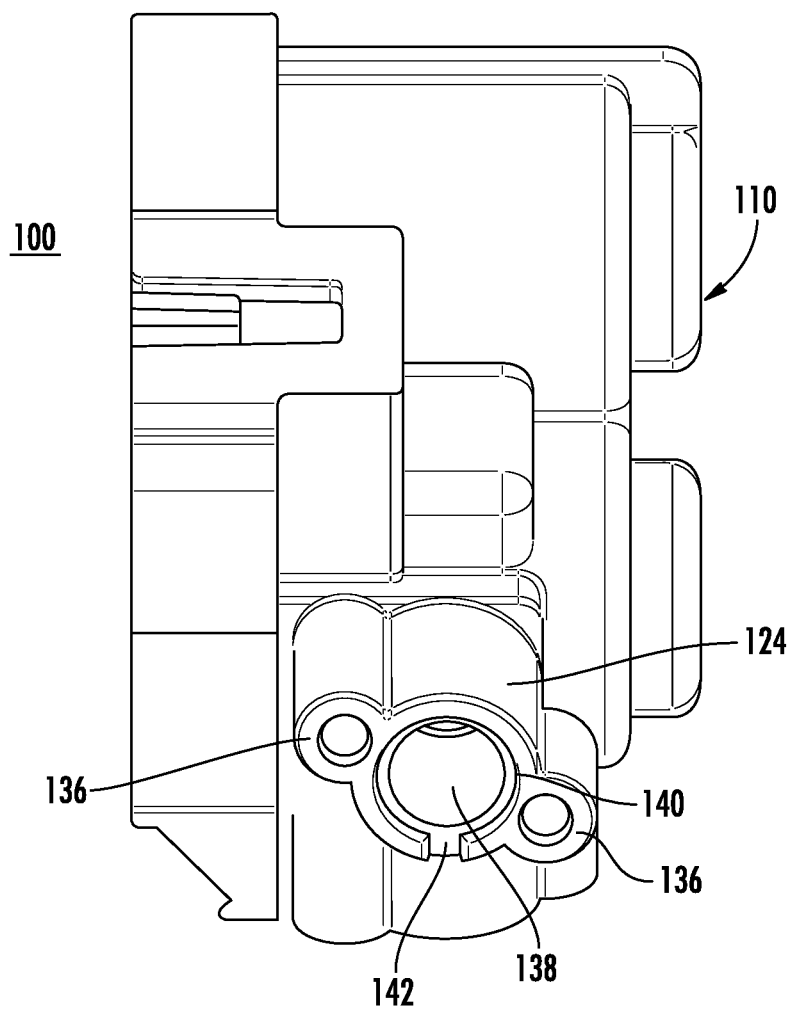
Figure 12:
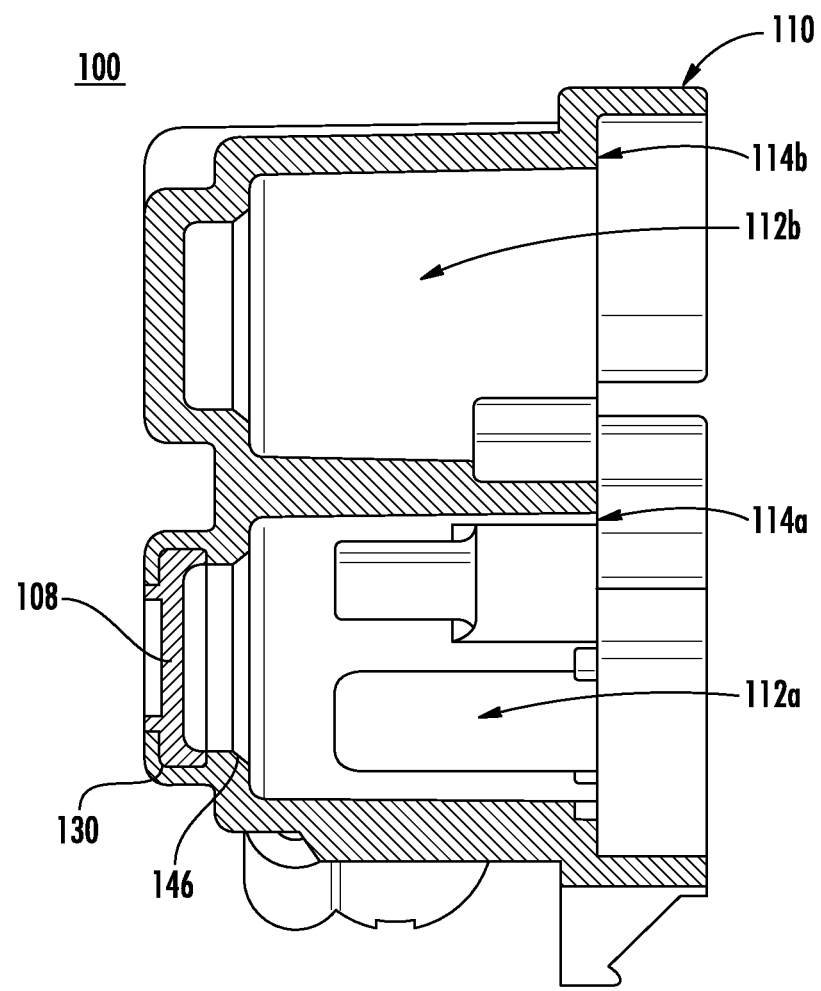
Figure 13:
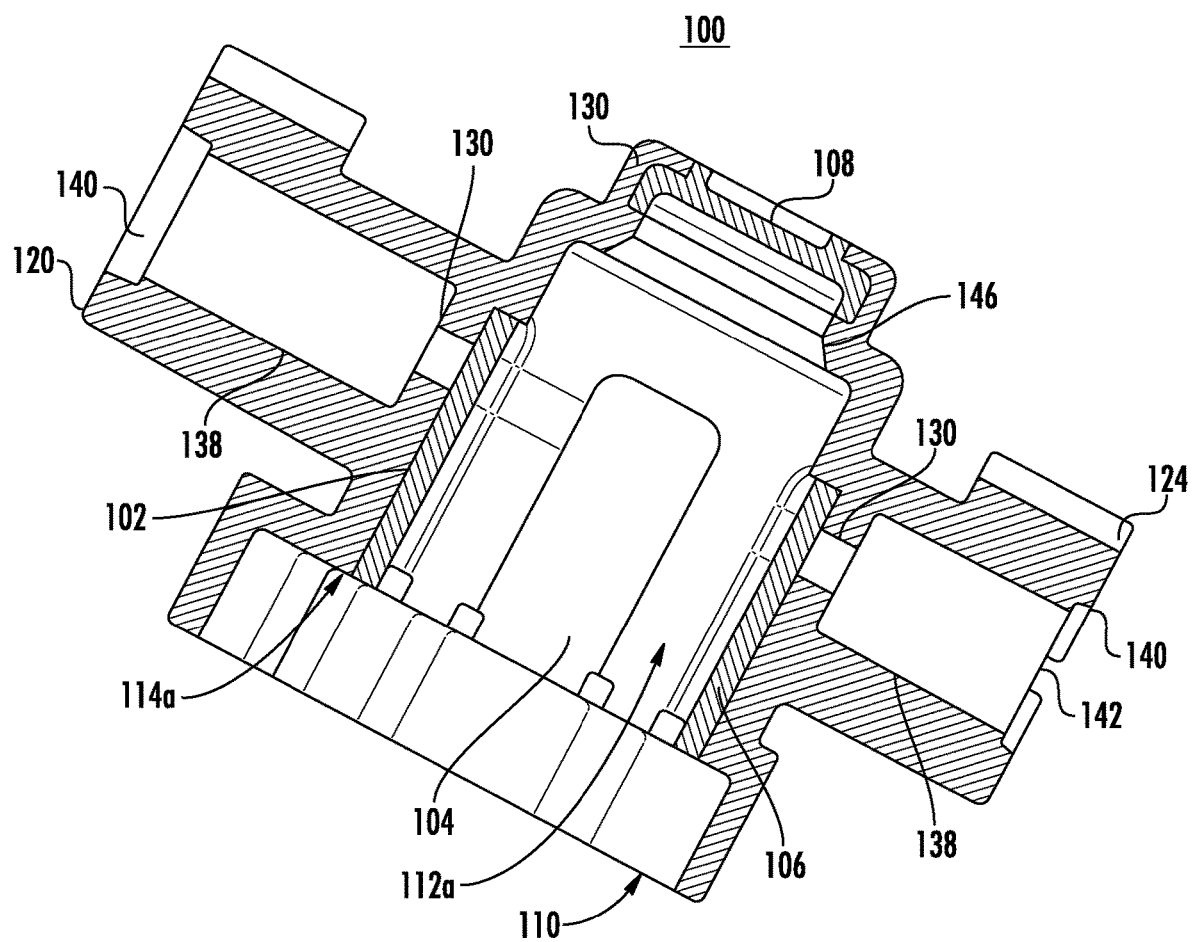
Figure 14:
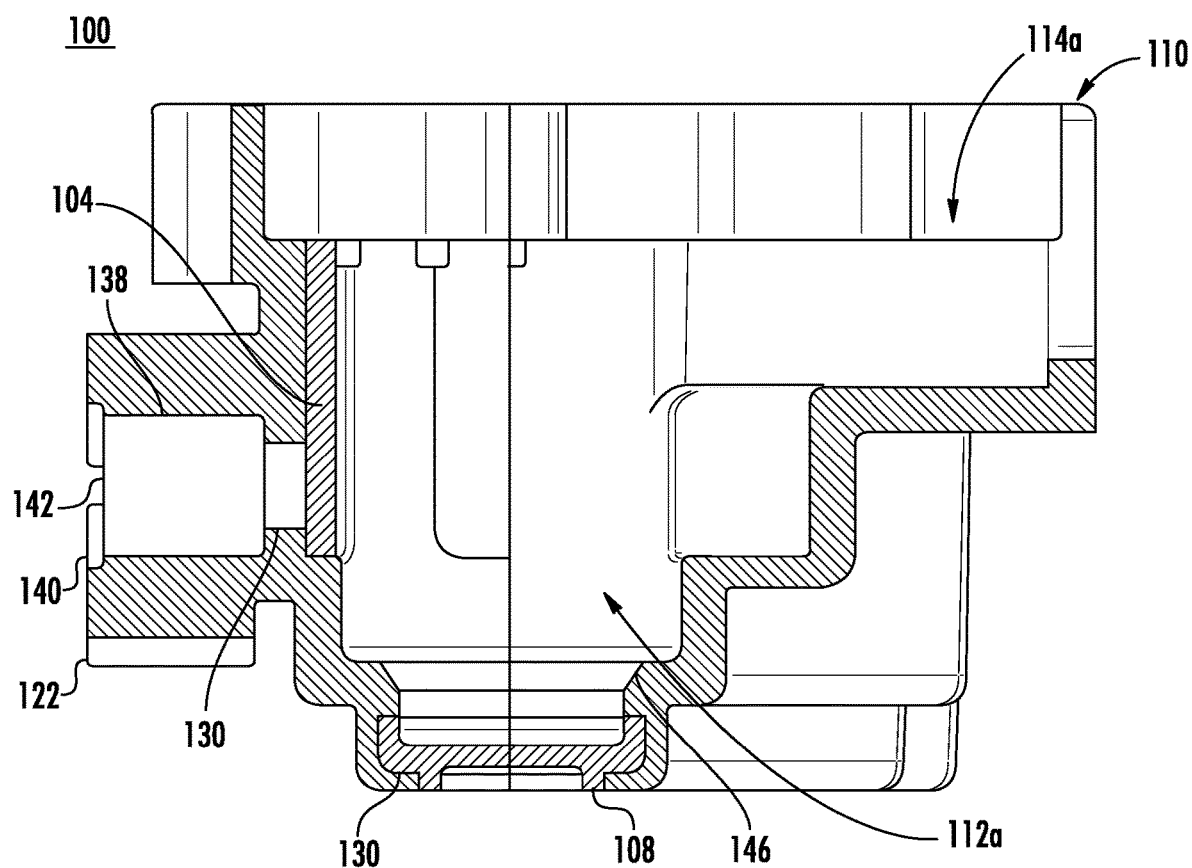
Figure 15:
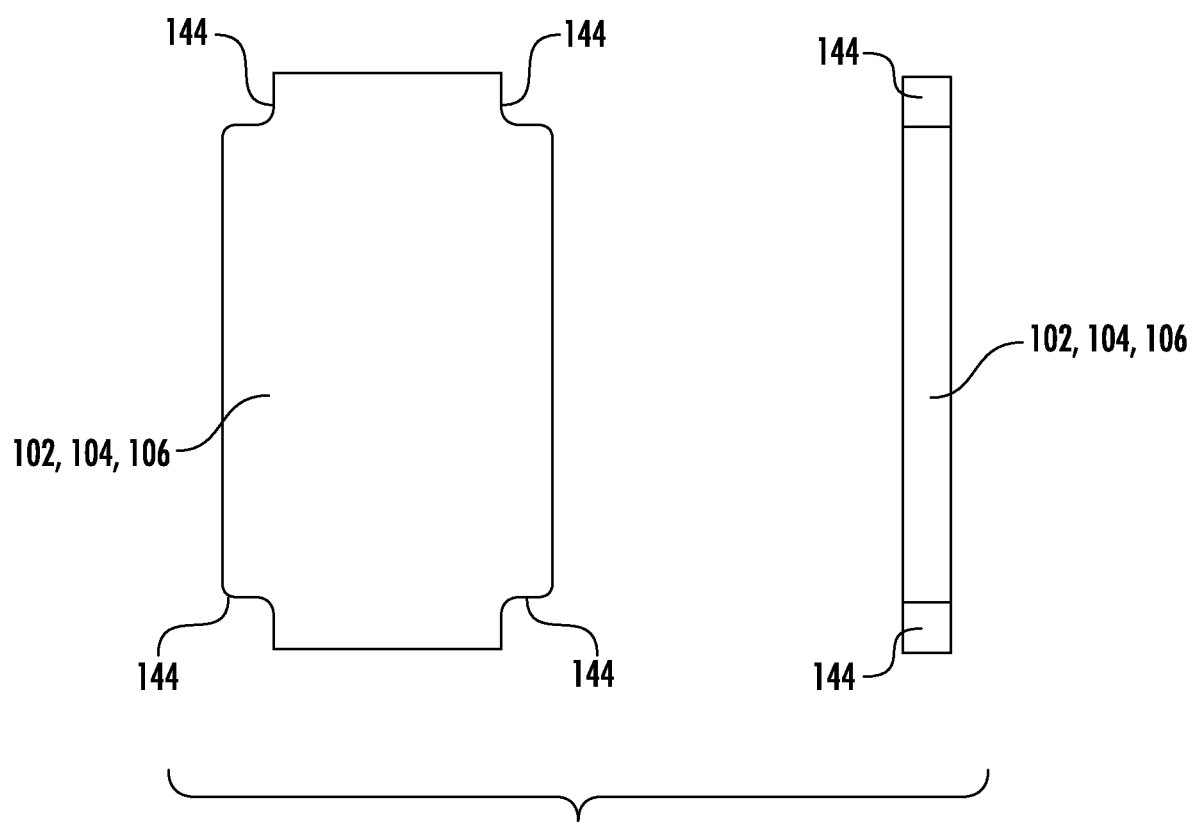
Figure 16:
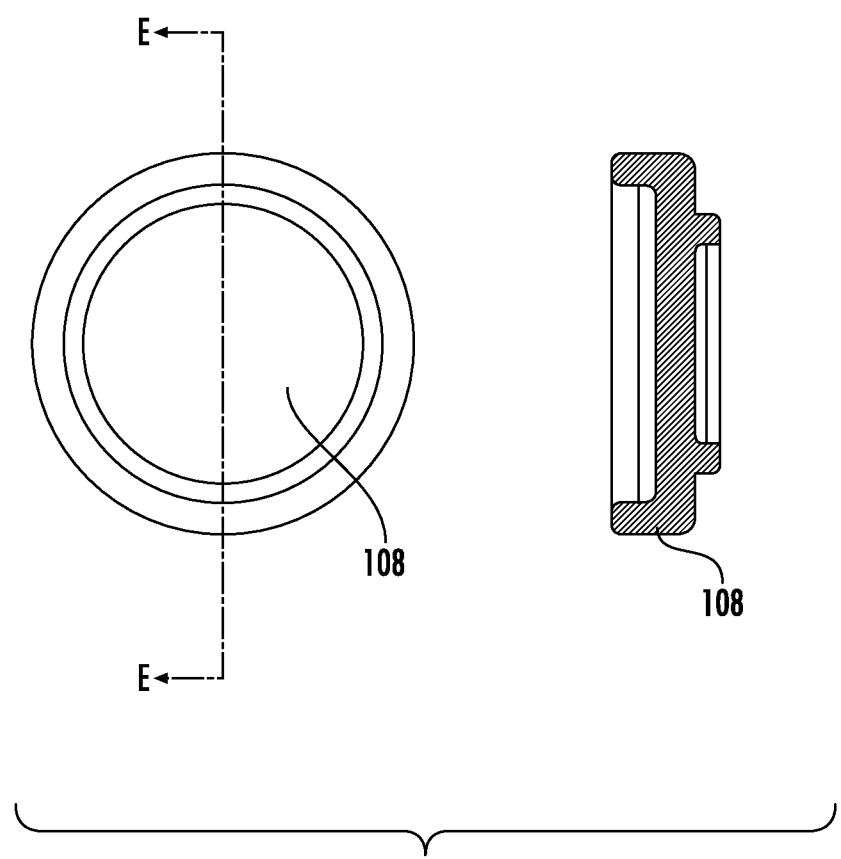
Figure 17:
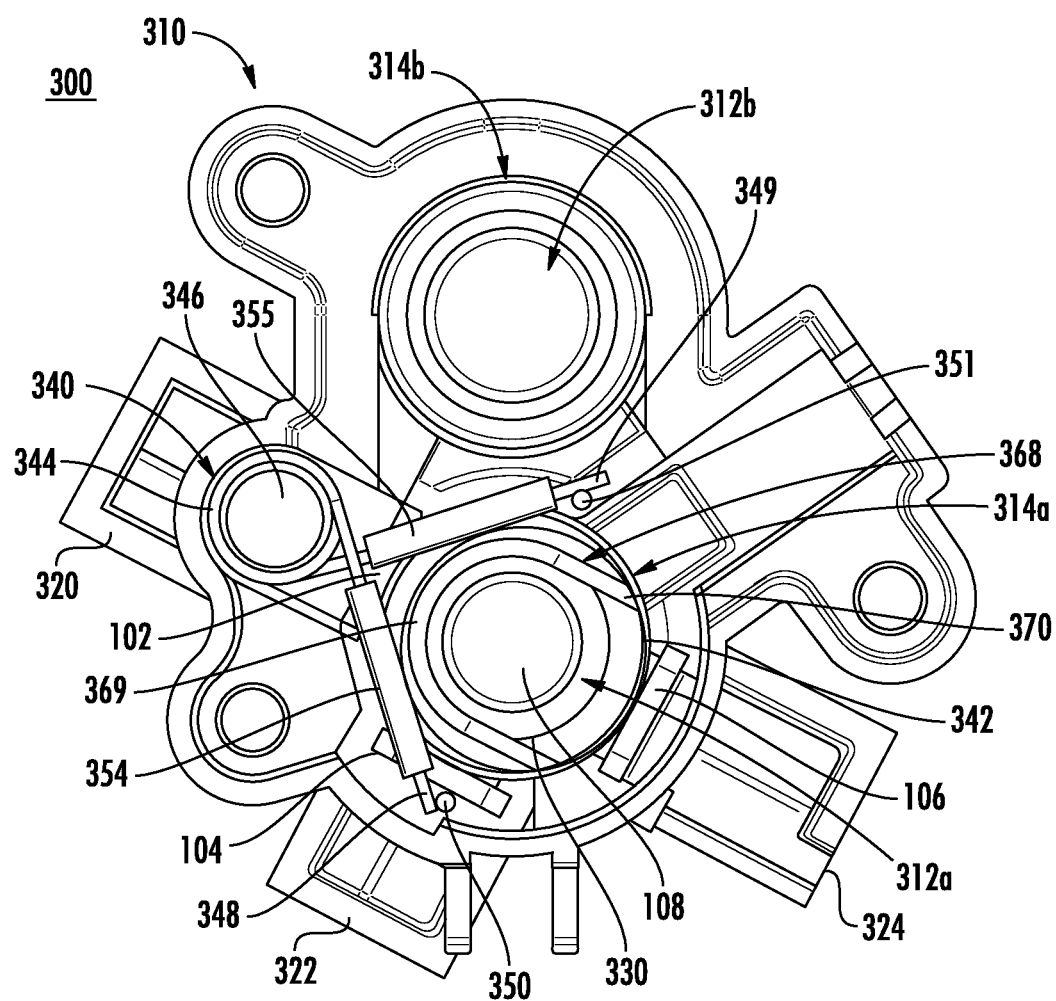
Figure 18:
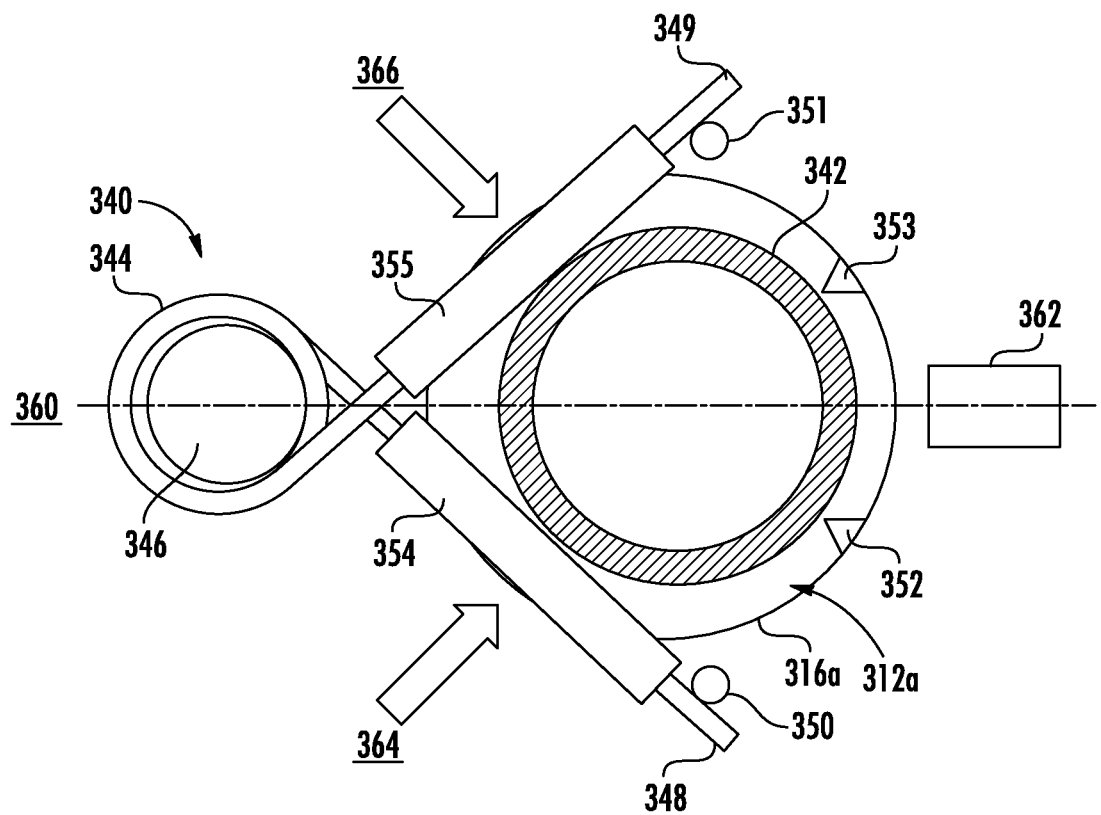
Figure 19:
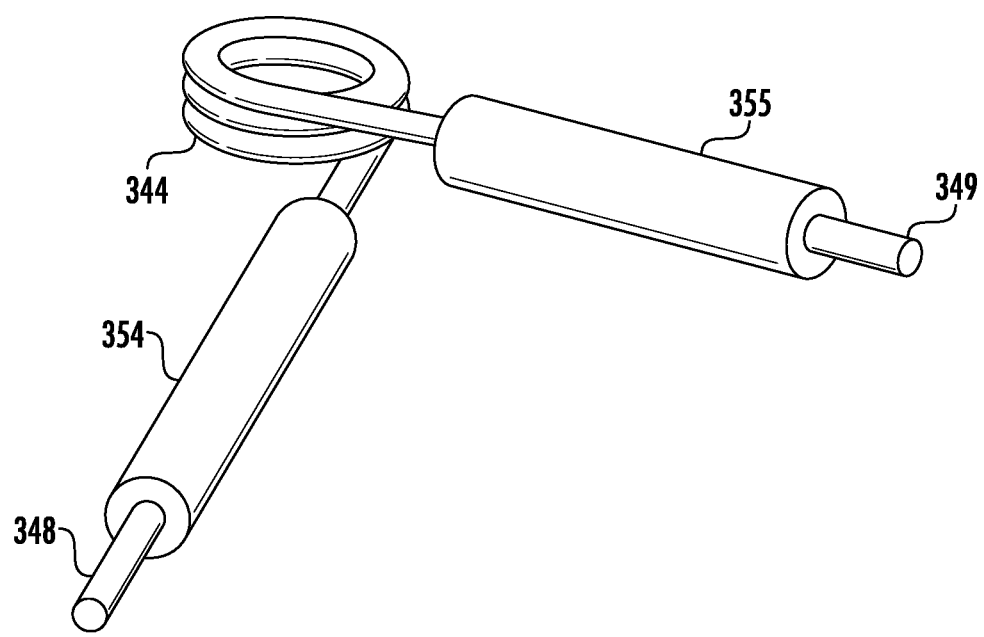
Figure 20:
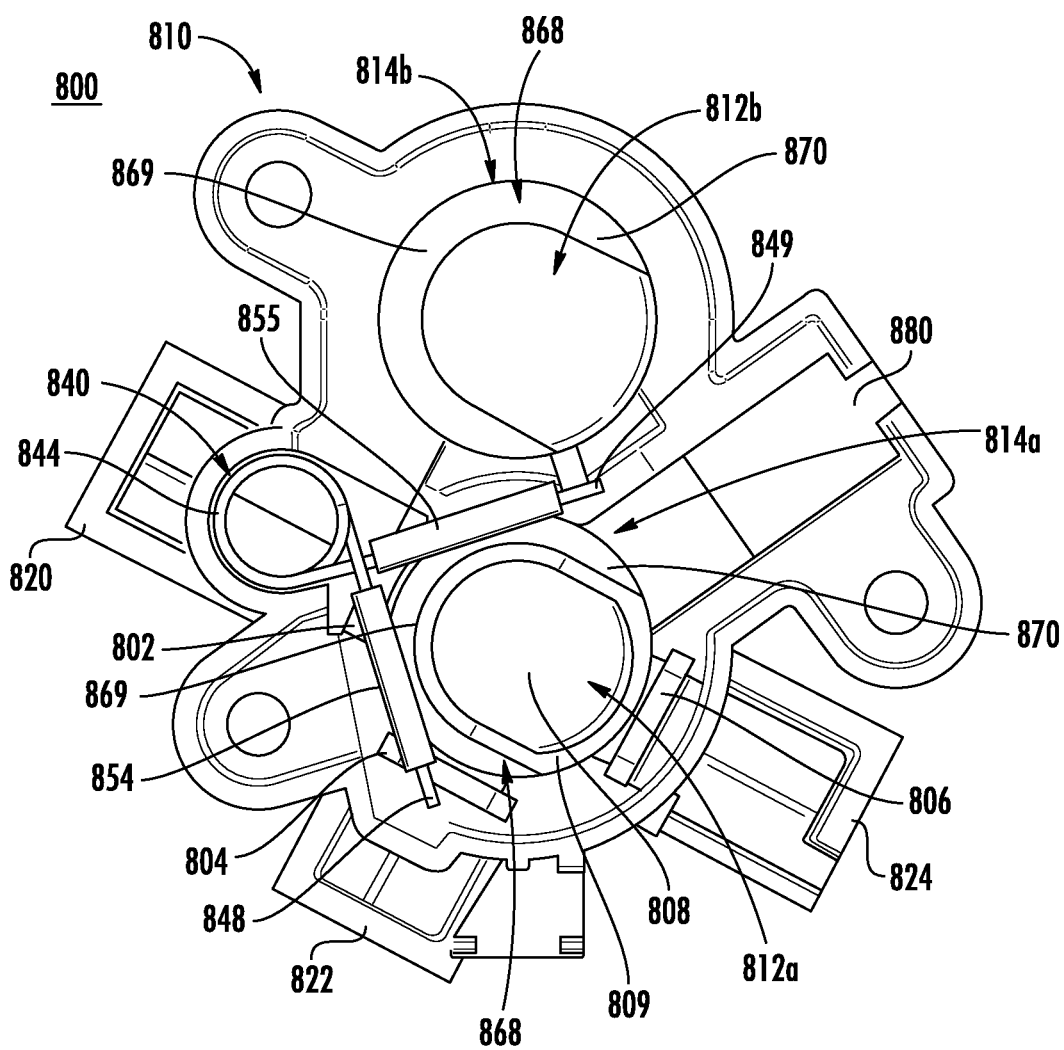
Figure 21:
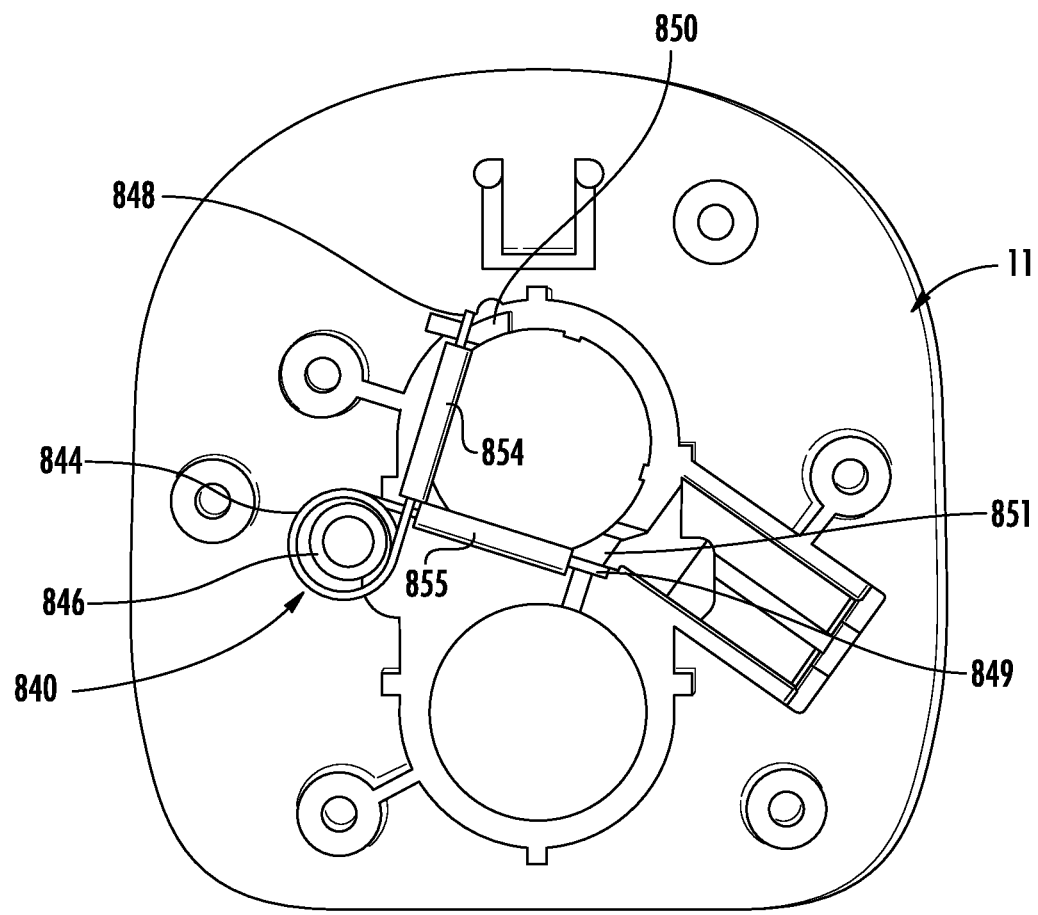
Figure 22:
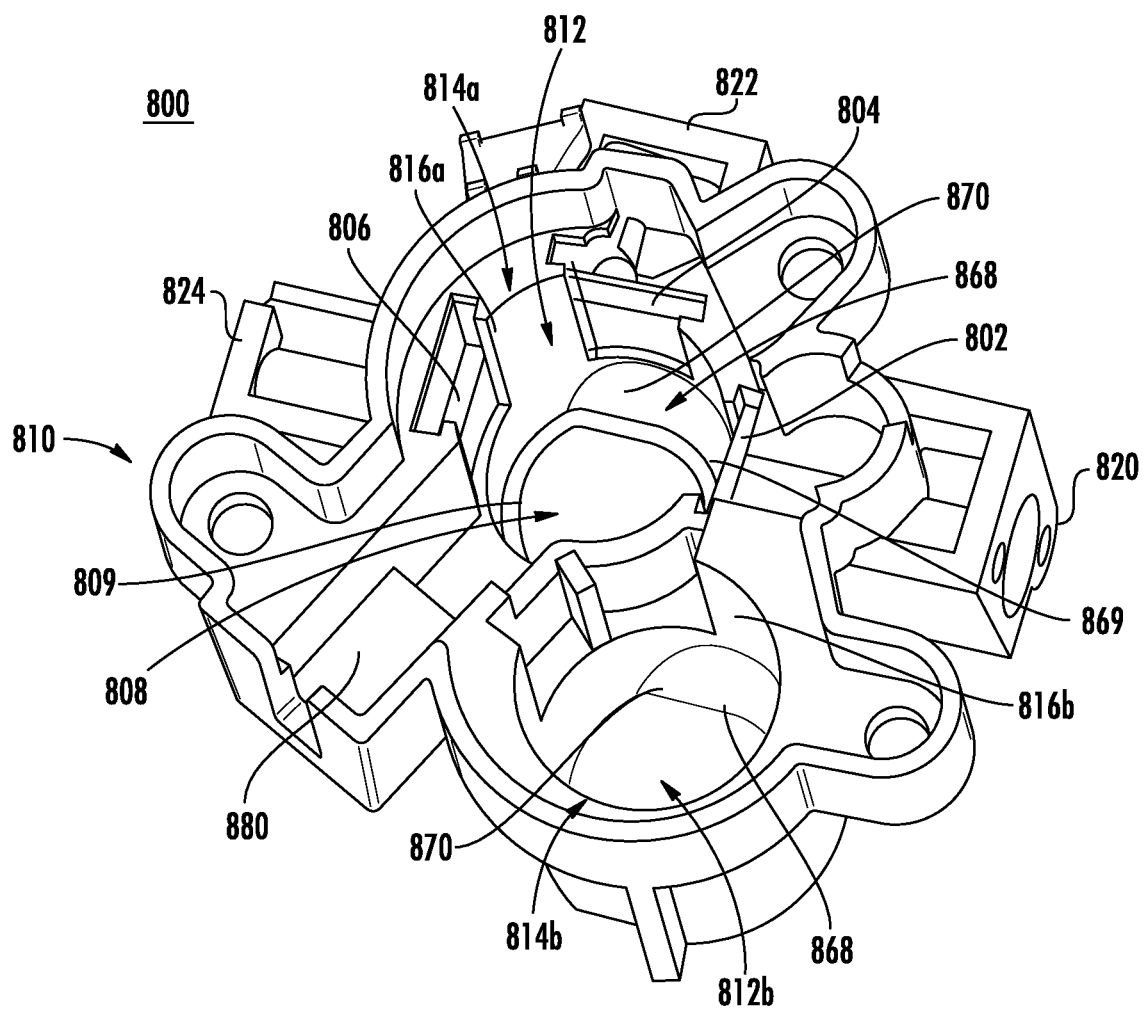
Figure 23:
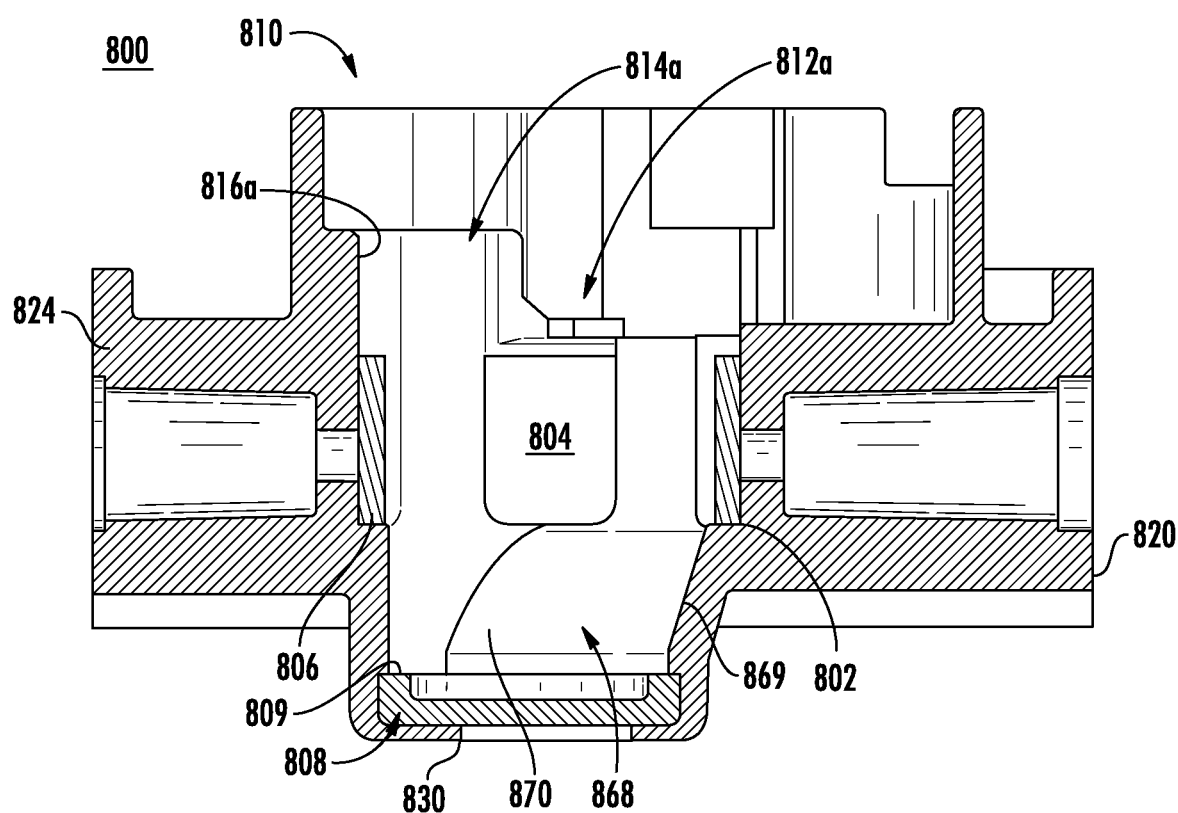
Figure 24:
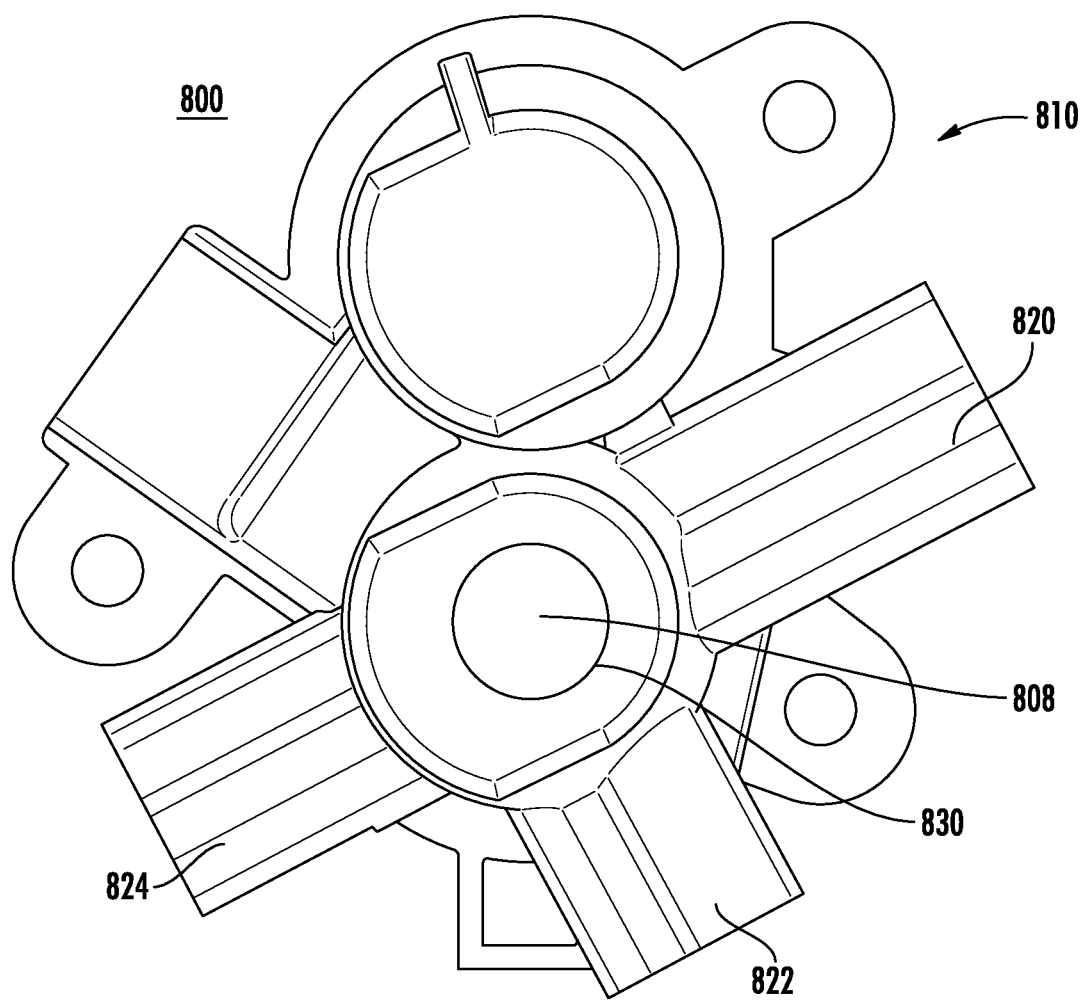
Figure 25:
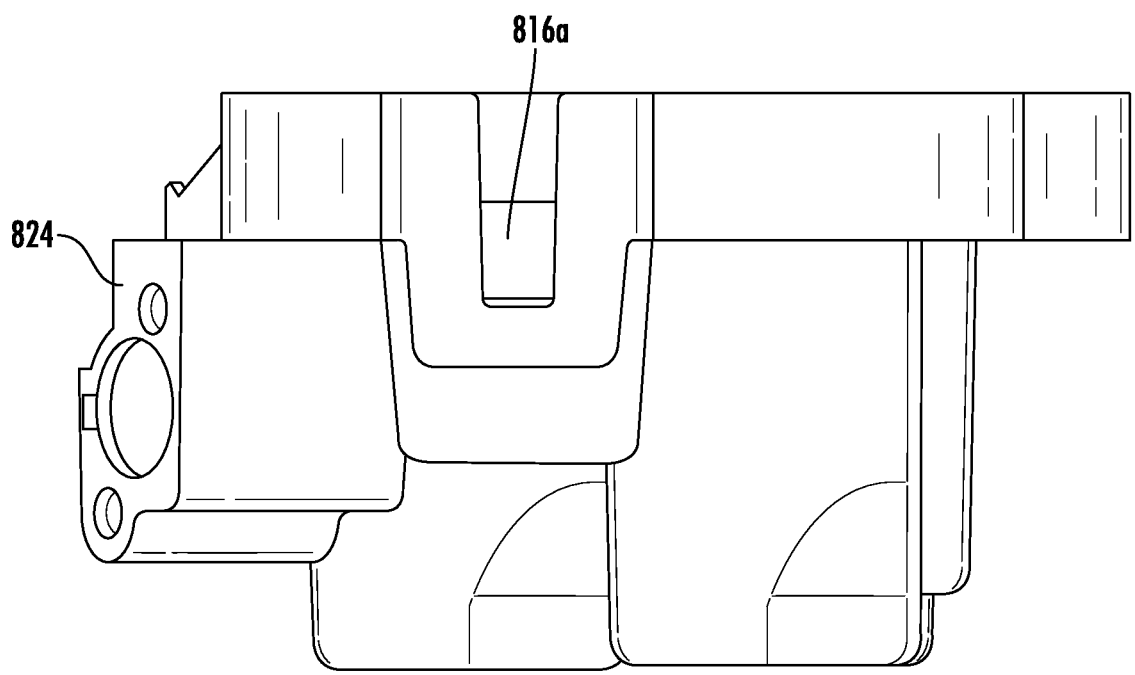
Figure 26:
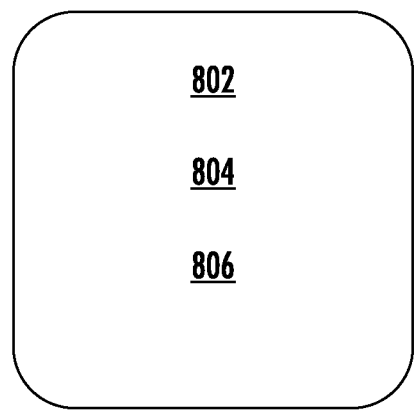
Figure 27:
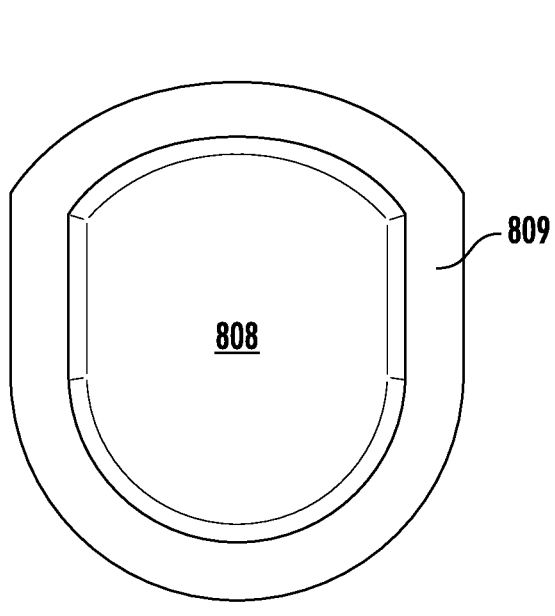
Figure 28:
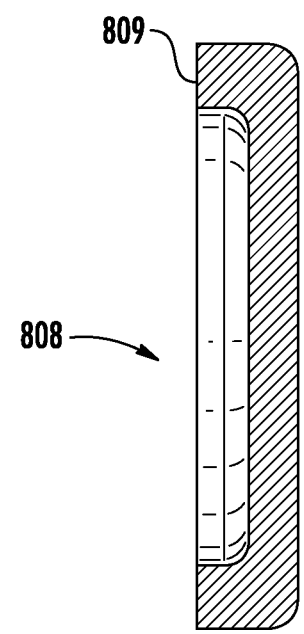

Having thus described the disclosure in general terms, reference will now be made to the accompanying drawings, which are drawn to scale except as noted otherwise, and wherein:

FIG. 1 is a perspective view of an instrument according to an example embodiment;

FIG. 2 is a not-to-scale illustration of the relative positioning of the optical density emitters and sensors relative to the sample tube according to an example embodiment;

FIG. 3 is a perspective view of an optical test platform according to an example embodiment;

FIG. 4 shows the optical paths of light traveling through the optical test platform of FIGS. 2 and 3;

FIG. 5 is a top plan view of the optical test platform according to an example embodiment;

FIG. 6 is a bottom plan view of the optical test platform according to an example embodiment;

FIG. 7 is a side view of the optical test platform according to an example embodiment;

FIG. 7A is a detail view of the mount shown in FIG. 7;

FIG. 8 is another side view of the optical test platform according to an example embodiment;

FIG. 8A is a detail view of the mount shown in FIG. 8;

FIG. 9 is another side view of the optical test platform according to an example embodiment;

FIG. 9A is a detail view of the mount shown in FIG. 9;

FIG. 10 is another side view of the optical test platform according to an example embodiment;

FIG. 11 is another side view of the optical test platform according to an example embodiment;

FIG. 12 is a cross-section taken across reference orientation A-A shown in FIG. 5;

FIG. 13 is a cross-section taken across reference orientation B-B shown in FIG. 5;

FIG. 14 is a cross-section taken across reference orientation C-C shown in FIG. 5;

FIG. 15 is a window according to an example embodiment;

FIG. 16 is a lower window according to an example embodiment;

FIG. 17 is a top plan view of an optical test platform according to an example embodiment;

FIG. 18 is a not-to-scale simplified top plan view of an optical test platform according to an example embodiment;

FIG. 19 is a perspective view of a spring with rollers according to an example embodiment;

FIG. 20 is a top plan view of an optical test platform according to an example embodiment;

FIG. 21 is a bottom plan view of a housing for an optical density instrument according to an example embodiment;

FIG. 22 is a perspective view of the optical test platform of FIG. 20;

FIG. 23 is a cross section of the optical test platform of FIG. 20;

FIG. 24 is a bottom plan view of the optical test platform of FIG. 20;

FIG. 25 is a side view of the optical test platform of FIG. 20;

FIG. 26 is a window according to an example embodiment;

FIG. 27 is a top plan view of a lower window according to an example embodiment; and FIG. 28 is a cross section of the lower window of FIG. 27.

DETAILED DESCRIPTION

The present invention will now be described more fully hereinafter with reference to the accompanying drawings in which some but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The instruments and accompanying methods and systems described herein are directed to an improved optical test platform for an optical density instrument. As described herein, the optical test platform may facilitate optical interrogation of a sample by supporting and positioning the sample in optical alignment with one or more optical emitters and optical density sensors. In a preferred embodiment, a liquid sample may be held in a sample tube, and the tube may be supported and positioned by the optical test platform to facilitate the interrogation. One readout for this measurement of turbidity and/or concentration of microorganisms in the liquid that can be obtained is known as a McFarland value. This value is obtained using a series of McFarland standards, which are a series of known concentrations of solutions that are used to prepare a standard curve in order to determine the concentration of particles in an unknown sample.

FIG. 1 shows an example optical density instrument in accordance with the present invention. In the depicted embodiment, the optical instrument 1 holds two sample tubes 15 for optical density testing. The optical instrument 1 may comprise a handheld unit 10 and a base station 20. In some embodiments, the handheld unit is battery operated for convenience and flexibility and includes the optical test platform detailed herein. The handheld unit 10 may transmit data to the base station 20 via Bluetooth® or another wireless or wired protocol that permits real time data transfer. The base station 20 may then be wire or wirelessly connected to a computer for receiving the optical density data in real time. In some embodiments, the handheld unit 10 may hold two sample tubes or a fused, dual sample tube 15. Further details regarding the instrument, its structure, and operation may be found in U.S. Provisional Application No. 62/487,796, entitled "OPTICAL DENSITY INSTRUMENT AND SYSTEMS AND METHODS USING THE SAME," which application is incorporated by reference herein in its entirety.

With reference to FIG. 2, an illustration of the optical components 22, 24, 26, 28 and a sample tube 15 of the optical density instrument are shown. The optical density components may include at least one emitter 22 (e.g., an LED, photodiode, or other light source) for emitting light into the sample tube 15 and at least one sensor 24, 26 (e.g., a photodetector, CCD, CMOS, or any other sensor capable of receiving incident light and outputting a signal indicative of the light's intensity) for receiving light that passes through the sample. In the illustrated embodiment of FIG. 2, one emitter 22 and two sensors 24, 26 are used to generate an accurate optical density reading of the sample. In operation, the emitter 22 may transmit light into the sample and a portion of the transmitted light passes through the sample to a first sensor 24 positioned opposite the emitter 22 relative to the sample tube and oriented collinearly with the emitter, while a second portion of the transmitted light reflects off of the sample and is collected by a second sensor 26 offset from the axis spanning the emitter 22 and first sensor 24.

In particular, the first sensor 24 may be oriented collinearly relative to the axis 30 of the emitter 22 and may be oriented 180 degrees offset from the emitter 22 with respect to the axis 32 of the sample tube 15. In some embodiments, the second sensor 26 may be positioned 90 degrees about the radial circumference of the sample tube 15 from both the emitter 22 and first sensor 24 on a perpendicular axis 34 to collect reflected light. In some embodiments, the second sensor 26 may be positioned at an acute angle to the axis 30 of the emitter 22. In some other embodiments, the second sensor 26 may be positioned at an oblique angle to the axis 30 of the emitter 22. In some embodiments, a perpendicularly-oriented nephelometric sensor may The emitter 22 may be configured to transmit the light perpendicular to the surface of the tube 15 and, in some embodiments, perpendicular to the longitudinal axis 32 of the sample tube 15. The portion of light collected by the first, pass-through sensor 24 may be called the "density" reading, and the portion of light collected by the second, reflective sensor 26 may be called the "nephelometric" reading. The optical density instrument may then combine the density and nephelometric signals from each sensor 24, 26 to generate a McFarland reading (or other optical measurement) of the sample. Further details regarding the operation of the sensors, including calibration, zeroing, and data collection, may be found in U.S. Provisional Application No. 62/487,736, entitled "METHOD, APPARATUS, AND COMPUTER PROGRAM PRODUCT FOR CONTROLLING COMPONENTS OF A DETECTION DEVICE," which application is incorporated by reference herein in its entirety.

With continued reference to FIG. 2, in some embodiments, a practitioner may wish to observe the sample directly during optical testing. In such embodiments, the optical components may further include an illumination light 28 (e.g., an LED or other light source) configured to emit light upwardly into the sample. Further details regarding the operation of the illumination light, and corresponding methods of using and reducing interference from the illumination light, may be found in U.S. Provisional Application No. 62/487,736, entitled "METHOD, APPARATUS, AND COMPUTER PROGRAM PRODUCT FOR CONTROLLING COMPONENTS OF A DETECTION DEVICE," which application is incorporated by reference herein in its entirety.

With reference to FIGS. 3-14, the instrument includes the optical test platform 100 to structurally support and align each of the optical components 22, 24, 26, 28 with the sample tube 15. Existing optical density instruments suffer from a number of deficiencies with respect to the alignment, support, and operation of their traditional optical elements. For example, it is preferred to seal the sample support area of the optical test platform from the electronics to avoid spillage issues, and thus, the optical test platform 100 positions the optical components 22, 24, 26, 28 outside of the sample tube 15 support area (e.g., cavity 112a shown in FIG. 3). This then requires the optical components 22, 24, 26, 28 to be able to optically communicate through the shell of the optical test platform. If the entire optical test platform 100 is molded as a single piece, the piece must be at least partially transparent to allow the light to propagate through the platform and sample. If, however, the entry point for the light transmitted by the emitter 22 into the optical test platform 100 is allowed to optically communicate through a shell 110 of the instrument with the exit point of the light received by either sensor 24, 26, the accuracy of the instrument may deteriorate. Said differently, if the structure of the optical test platform 100 allows light to travel from the emitter 22 to one or both of the sensors 24, 26 without passing through the sample 15, interference may negatively affect the test results.

FIGS. 3-14 show various views of an example optical test platform 100. With reference to FIG. 3, a perspective view of the optical test platform 100 is shown in accordance with embodiments detailed herein. The optical test platform 100 of the present disclosure may include separate windows 102, 104, 106, 108 located within and embedded into the shell 110 of the test platform.

The shell 110 may be molded of an opaque or semi-opaque material. In some further embodiments, the shell 110 may be formed of a dark color polymer. In yet some further embodiments, the shell 110 may be formed of a black polymer. The windows 102, 104, 106 allow light to pass through the shell 110 at generally perpendicular angles to the surface of the window, with the shell material prohibiting light from propagating through the shell itself. The shell 110 may define one or more cavities 112a, 112b (collectively "112") therein. The cavities 112 may receive the sample tubes 15 (shown in FIGS. 1-2) through an upper aperture 114a, 114b (collectively "114"), and the sample tubes 15 may be supported by the shell. In some embodiments, the cavities 112 may be substantially cylindrical, and in some embodiments, the cavities 112 may be bounded by one or more walls 116a, 116b.

The shell 110 may hold any of several configurations of sample tubes 15. For example, in the depicted embodiment of FIG. 3, the shell 110 includes two cavities 112a, 112b configured to receive two corresponding sample tubes 15. The depicted embodiment is configured to test one of the two tubes (e.g., the optical components only interrogate one of the two cavities, cavity 112a), while the second cavity 112b is left for convenience to hold a second tube. For example, once the optical density of the tube 15 in the first cavity 12a reaches a desired concentration, separate samples based on that concentration may be made in the second tube 15 (e.g., diluted versions of the original concentration based on the known concentration of the tube in the first cavity 112a, such as for antibiotic susceptibility testing). This dual sample tube configuration is useful for use with a dual-test tube or other fused sample tubes, where the two tubes should be kept together for study but need not be independently checked with optical density sensors. In some alternative embodiments, two or more optical components may be used to interrogate the second cavity 112b. Although the description herein refers to interrogating a single sample tube, these teachings may be readily applied to a second set of optical components operating on the second cavity 112b. In some alternative embodiments, the optical test platform may include only a single cavity for testing a single sample tube, or in some embodiments, greater than two sample tubes may be used with one, two, or more sets of optical components for interrogating the respective tubes. The cavities 112 may include a support ring 146 or fillet for engaging and supporting the sample tubes 15.

The optical test platform 100 may include one or more mounts 120, 122, 124 for engaging and supporting the optical components (e.g., the emitter 22, first sensor 24, second sensor 26, and/or illumination light 28 shown in FIG. 2). In the embodiments shown in FIGS. 2-14, the first mount 120 may receive and engage the emitter 22, the second mount 122 may receive and engage the second sensor 26, and the third mount may receive and engage the first sensor 24. One of ordinary skill in the art will also appreciate, in light of this disclosure, that the mounts 120, 122, 124 and optical components 22, 24, 26, 28 may be reconfigured to any arrangement that satisfies the possible emitter-sensor relationships discussed herein. In some embodiments, the mounts 120, 122, 124 may be integrally molded with the shell 110, and in some other embodiments, the mounts 120, 122, 124 may be separately attached to the shell.

FIGS. 7-7A show side views of the first mount 120 viewed from the exterior of the optical test platform, and FIG. 13 (left side) shows a cross-sectional view of the first mount 120. FIGS. 9-9A show side views of the second mount 122 viewed from the exterior of the optical test platform, and FIG. 14 shows a cross-sectional view of the second mount 122. FIGS. 8-8A show side views of the third mount 124 viewed from the exterior of the optical test platform, and FIG. 13 (right side) shows a cross-sectional view of the third mount 124.

With reference to the respective figures in the aforementioned paragraph, each of the mounts 120, 122, 124 may include a central bore 138 into which a portion of the optical receiving or transmitting elements of the respective optical components 22, 24, 26, 28 (shown in FIG. 2) may be inserted. At a distal end of the central bore 138, opposite the cavity 112a, each mount 120, 122, 124 may define a notch 140 for receiving a portion of the optical components therein. The notch 140 may further define a keyway 142 for rotationally aligning the optical component with in a respective bore 138, by engaging a corresponding notch in the optical component.

At a proximate end of the central bore 138 of each mount 120, 122, 124, the shell 110 may define an aperture 130 to allow light to pass through the shell. The aperture 130 may optically connect the cavity 112a with the optical components 120, 122, 124 to allow the optical components to respectively transmit light into the cavity from outside the cavity, or receive light outside the cavity from inside the cavity. In some embodiments, the aperture 130 may have a narrower diameter than the central bore 138, which may assist with positioning the optical components by providing a predefined stop point for the components, may reduce interference or noise from being received by the sensors 24, 26 by narrowing the opening through which light passes into the optical component, and may structurally support the window 102, 104, 106 by preventing the optical component from acting on the window.

The shell may further define an aperture 130 at a lower end of the cavity 112a opposite the upper aperture 114a. In some embodiments, a window 108 may be embedded in the aperture 130 to allow the illumination light 28 (shown in FIG. 2) or another optical component to communicate with the cavity. In the embodiment depicted in FIGS. 3-14, the lower window 108 may allow the illumination light 28 (shown in FIG. 2) to illuminate the sample tube 15 (shown in FIG. 2).

The windows 102, 104, 106, 108 may be embedded in the shell 110 to allow optical communication between outside the cavity 112a, including the interior of the bore 138, and the interior of the cavity 112a via the aperture 130. As used herein, the term "embedded" refers to the permanent (at least requiring damage, plastic deformation, and/or destruction) affixation between the window and shell without requiring (although not precluding) adhesives, such that the physical structure of the shell retains the window. In some embodiments, no adhesives or fasteners may be used to embed the windows 102, 104, 106, and 108 within the shell 110. In some embodiments, the windows 102, 104, 106, 108 are embedded into the shell 110 by molding the shell around the windows to fix them within the permanently-molded structure of the shell. One of ordinary skill in the art will appreciate, in light of the present disclosure, that the shell 110 may be made of one or several pieces, which may be molded together or attached separately without departing from the scope of the present disclosure. For example, in some other embodiments, the shell may be machined or 3D printed and shaped or snapped around the windows.

In some embodiments, the aperture and window for each respective optical component may be generally coplanar, such that the window is positioned within the aperture (e.g., as shown in FIGS. 12-14 between the aperture 130 and lower window 108). In some other embodiments, as shown in FIGS. 12-14, the window may rest axially against the aperture in a separate pocket (e.g., as shown in FIGS. 12-14 between the aperture 130 and sensory windows 102, 104, 106). In any embodiment, the embedding process may seal the window 102, 104, 106 and shell 110 such that fluid may not pass through the aperture 130 and damage the electronics of the instrument. In some embodiments, a rib or flange of the shell 110 may overlap the window about its edges to encapsulate the edges of the window and provide a seal and fixation. With reference to FIGS. 15 and 16, diagrams of the sensory windows 102, 104, 106 and the lower window 108 are shown respectively. In some embodiments, with reference to FIG. 15, the sensory windows 102, 104, 106 may be substantially rectangular, with a longer vertical dimension than horizontal dimension. The sensory windows 102, 104, 106 may include notches 144 for improving fixation between the shell 110 and windows.

Referring back to FIGS. 3-14, each of the mounts 120, 122, 124 may include one or more attachment points 136 to which the optical components may be attached. For example, FIGS. 7-7A show attachment points 136 (e.g., screw or bolt holes) of the first mount 120 to which the emitter 22, or one of the sensors 24, 26 (shown in FIG. 2) may be mounted. Similarly, FIGS. 9-9A show attachment points 136 (e.g., screw or bolt holes) of the second mount 122 to which the emitter 22, or one of the sensors 24, 26 (shown in FIG. 2) may be mounted. Further, FIGS. 8-8A show attachment points 136 (e.g., screw or bolt holes) of the second mount 122 to which the emitter 22, or one of the sensors 24, 26 (shown in FIG. 2) may be mounted. In some embodiments, the attachment points 136 may be on opposite sides of the bore 138 of the mounts 120, 122, 124.

The mounts 120, 122, 124; the central bores 138; the apertures 130; and the sensory windows 102, 104, 106 may each be configured to facilitate the operation of the emitters and/or sensors described herein. In some embodiments, the mounts 120, 122, 124; the central bores 138; the apertures 130; and/or the sensory windows 102, 104, 106 may be oriented coaxially with the respective emitters or sensors affixed thereto. For example, first mount 120 shown in FIG. 3 may engage the emitter 22 shown in FIG. 2, and in such case, the first mount 120 (including bore 138 and notch 140), the corresponding aperture 130, and the first window 102 may each be oriented along the axis 30 of the emitter 22 shown in FIG. 2. In such embodiments, the bore 138 and aperture 130 may be cylindrical and may have a longitudinal axis that is coaxial with the axis 30 of the emitter 22. Similarly, the first window 102 may have a surface whose normal vector is aligned with the axis 30 of the emitter 22, such that light may pass into the window in a generally perpendicular direction to reduce distortion.

Similarly, the shell 110 may include a mount for the illumination light 28, which may also align the illumination light 28 with the components of the mount and the window 108. The illumination light 28 may thereby illuminate the sample tubes 15 for observation by the practitioner. In the embodiment shown in FIG. 3, the illumination light 28 (shown in FIG. 2) may be oriented upwardly into the cavity 112a to illuminate the sample tube 15 (shown in FIG. 2) from beneath. The illumination light 28 may be oriented perpendicular to the axes of the emitter 22, first sensor 24, and/or second sensor 26. For example, with reference to FIG. 2, the illumination light 28 is oriented along the central axis 32 of the sample tube 15.

The aforementioned alignment may also be provided with respect to the first sensor 24 and the third mount 124 and corresponding aperture 130, and with respect to the second sensor 26 and the second mount 122 and corresponding aperture 130. For example, the bore 138 and aperture 130 associated with the third mount 124 may be cylindrical and may have a longitudinal axis that is coaxial with the axis 30 of the emitter 22 (also corresponding to the axis of the first sensor 24 based on their collinearity). The third window 106 may also have a surface whose normal vector is aligned with the axis 30 of the emitter 22, such that light may pass into the window in a generally perpendicular direction to reduce distortion. Moreover, the bore 138 and aperture 130 associated with the second mount 122 may be cylindrical and may have a longitudinal axis that is coaxial with the axis 34 of the second sensor 26. The second window 104 may also have a surface that is perpendicular to the axis 34 of the second sensor 26, such that light may pass into the window in a generally perpendicular direction to reduce distortion. As discussed above, the axis 30 of the emitter 22 and first sensor 24 may be collinear and each may be offset from and, in some embodiments, perpendicular to the axis 34 of the second sensor 26. As also discussed above, the emitter 22 and sensors 24, 26 may be attached to any combination of mounts 120, 122, 124 that facilitates either density sensing (e.g., collinear placement of the emitter and sensor), nephelometric sensing (e.g., offset placement of the emitter and sensor), or both. For example, the emitter 22 may be attached to the third mount 124, with the first sensor 24 being attached to the first mount 120 and the second sensor 26 being attached to the second mount 122.

With reference to FIG. 4, an illustration of the optical coupling of the emitters and sensors is shown. In the depicted embodiment of FIG. 4, the emitter 22 (shown in FIG. 2) would be attached to the first mount 120, the first sensor 24 (shown in FIG. 2) would be attached to the third mount 124, and the second sensor 26 (shown in FIG. 2) would be attached to the second mount 122. In operation, the emitter 22 may emit light 150 into the cavity 112a. A first portion of the light 152 may be reflected from the sample in the cavity 112a and received by the nephelometric second sensor 26, and a second portion of the light 154 may pass through the sample in the cavity 112a and be received by the density first sensor 24. In the depicted embodiment, the first window 102, first mount 120, third window 106, and third mount 124 are arranged collinearly, and the second window 104 and second mount 122 are perpendicular to the axis of the first window 102, first mount 120, third window 106, and third mount 124. Thus, in the depicted embodiment, the emitter 22 and first sensor 24 would be arranged collinearly, and the second sensor 26 would be arranged perpendicular to the emitter 22 and first sensor 24.

Although the nephelometric 152 and density 154 signals are shown diverging at the center of the sample, the reflection and dispersion of the emitted light 150 may gradually occur across the length of the cavity 112a assuming an equal distribution of the sample.

As used herein, the term "optical coupling" or "optically coupled" refers to two components or features between which light may travel. In some instances, one or more features, such as the windows 102, 104, 106, and 108 and the apertures 130 may facilitate optical coupling by allowing light to pass therethrough.

The windows 102, 104, 106, and 108 described herein may be made of any transparent or substantially transparent material, including glass or polymers. For example, in some embodiments, the windows 102, 104, 106, and 108 may be made of Lexan®. In some embodiments, the shell 110 may be made of polypropylene, polyphenylene ether (PPE) resin, polypropylene oxide (PPO), polystyrene, or blends thereof. For example, in some embodiments, the shell 110 may be made of Noryl®. In some embodiments, the windows 102, 104, 106, and 108 may be made of any optically clear material. The shell 110 may either be molded of an opaque material, or the shell material may be dyed (e.g., black) to prevent optical transmission through the shell's structure. In some embodiments, the shell 110 may be made of any material that blocks light. In some further embodiments, the shell 110 may be made of any moldable material that blocks light.

Referring back to FIG. 3, in some embodiments, the shell 110 may have a slot 200 configured to receive a switch therein. The switch may detect placement of the sample tube 15 in the cavity 112a to trigger the optical density measurements and/or illumination steps detailed herein. The switch may be a mechanical switch that includes an actuator arm protruding into the cavity 112a from the slot 200 to contact the sample tubes 15 when they are nearly completely inserted. In some embodiments, the switch may be an electromechanical switch whose lever arm deflects into an electrical contact for signaling the optical testing instrument to automatically begin interrogating the sample.

In some embodiments, a method of manufacturing the test platform 100 described herein may be provided. With reference to FIG. 3, the test platform 100 may include a shell 110 defining a cavity 112a for receiving a sample tube 15, a first aperture 130, and a second aperture 130. The first aperture 130 and the second aperture 130 may each be configured to optically couple the cavity 112a with an exterior of the shell. The test platform 100 may further include a first window 102 embedded in the shell 110. The first window 102 may seal the first aperture 130. Moreover, a second window 104, 106 may be embedded in the shell 110, wherein the second window 104, 106 may seal the second aperture 130. The first window 102 and the second window 104, 106 may each be configured to permit the optical coupling of the cavity 112a with the exterior of the shell. The first window 102 and the second window 104, 106 may be optically coupled via the cavity 112a, and the shell 110 may be configured to prohibit optical coupling between the first window 102 and the second window 104, 106 through the shell 110.

The method may include embedding the first window and the second window in the shell. In some embodiments, embedding the first window and the second window in the shell may include positioning the first window and the second window in a shell mold, and molding the shell around the first window and the second window, such that the first window and the second window may be embedded in the shell. In some embodiments, molding the shell around the first window and the second window may include molding an opaque material around the first window and the second window. In some further embodiments, molding the shell around the first window and the second window may include permanently affixing the first window and the second window to the shell without adhesives or fasteners.

In some embodiments, molding the shell may further include molding a first mount 120 for a first optical component and a second mount 122, 124 for a second optical component. The first mount 120 may be optically coupled with the first aperture 130 at the exterior of the shell 110. The second mount 122, 124 may be optically coupled with the second aperture 130 at the exterior of the shell 110. The first mount 120 may be configured to position the first optical component 22 to emit light into the cavity 112a through the first window 102 along a first axis 30.

In some embodiments, a second mount 124 may be configured to position the second optical component 24 to receive light from the cavity 112a through the second window 106 along a second axis 30, and the first axis and the second axis may be collinear. This embodiment may be called a density sensor and mount.

In some other embodiments, a second mount 122 may be configured to position the second optical component 26 to receive light from the cavity 112a through the second window 104 along a second axis 34, and the first axis and the second axis may not be collinear. This embodiment may be called a nephelometric sensor and mount.

Turning to FIG. 17, a second embodiment of the optical test platform 300 is shown. The optical test platform 300 may include a shell 310 with one or more mounts 320, 322, 324; an aperture 330; upper apertures 314a, 314b; and cavities 312a, 312b that may each be structured and operate in substantially the same manner as the example optical test platforms 100, 800 detailed herein. Moreover, embodiments of the optical test platform 300, or portions thereof, may be incorporated into or substituted for portions of the optical test platforms 100, 800 detailed herein.

With continued reference to FIG. 17, the optical test platform 300 may include at least one spring 340 that urges a sample tube 342 to a predetermined position within one or more of the cavities 312a, 312b. In the embodiment depicted in FIG. 17, the optical test platform 300 includes a spring 340 configured to bias a sample tube 342 towards a window 106. The depicted spring 340 includes a coiled wire 344 disposed around a post 346 and two legs 348, 349 defining the respective ends of the wire.

The spring 340 may operate as a helical torsion spring, such that the helical coiled wire 344 is twisted about the axis of the coil (e.g., an axis extending perpendicular to the page of FIG. 17) by bending moments applied at the legs 348, 349. In such embodiments, the coiled wire 344 may elastically deform in response to a force on either or both legs 348, 349, and the coiled wire 344, when elastically deformed, may cause the legs 348, 349 to apply a force opposite the direction of the applied force. For example, the sample tube 342 may be inserted into the cavity 312a between the two legs 348, 349 which may cause an outward force (e.g., a force radially outward from the center of the cavity 312a) on the legs 348, 349 and a torsional torque on the coiled wire 344. The legs 348, 349 may apply an opposing inward force (e.g., a force radially inward towards the center of the cavity 312a) on the sample tube 342, caused by the torsional reaction torque of the coiled wire 344, which may push the sample tube toward the window 106.

In the depicted embodiment, the post 346 and spring 340 are disposed at the same side of the cavity 312a as the first mount 320, opposite the third window 106, to cause the spring to urge the sample tube 342 towards the third window as described herein. In some embodiments, the post 346 and spring 340 may be disposed at any other side of the cavity, including opposite the second window 104.

In some embodiments, a roller 354, 355 may be disposed on each of the respective legs 348, 349 of the spring 350, and the rollers 354, 355 may be slip fit or otherwise allowed to rotate about the legs 348, 349 to allow the sample tube 342 to move freely upwardly and downwardly (e.g., into and out of the page of FIG. 17). The legs 348, 349 may apply forces to the sample tube 342 perpendicular to the surfaces of the rollers 354, 355 (e.g., a force vector substantially intersecting a center of rotation of the rollers), while the rollers rotate when force is applied tangential to the surface of their surface. In this manner, gravity may retain the sample tube 342 vertically within the cavity 312a while still allowing the sample tube to be freely removed or inserted, and in the depicted embodiment, the spring 340 may hold at least a portion of the sample tube in position within the horizontal plane (e.g., the plane of the paper in FIG. 17). In some embodiments, the rollers 354, 355 may cause the legs 348, 349 to each apply a purely horizontal force to the sample tube 342. In some embodiments, the rollers 354, 355 may define generally hollow cylinders disposed about the legs 348, 349. In some embodiments, the rollers 354, 355 may be made from a low-friction material to prevent scratching the sample tube 342. For example, in some embodiments, the rollers 354, 355 may be made of PEEK (Polyether ether ketone), PTFE (Polytetrafluoroethylene), or Acetal (Polyoxymethylene).

With reference to FIG. 18, a simplified embodiment of the spring 340, sample tube 342, and surrounding components are shown for illustration purposes. In the depicted embodiment, the legs 348, 349 may apply forces 364, 366 on the sample tube 342 in directions that are at least partially towards a detector 362 and at least partially towards a center axis 360 bisecting the legs 348, 349. In some embodiments, the center axis 360 may extend between a diametric center of the post 346 and the detector 362. In some embodiments, the widthwise center of one or more windows (e.g., windows 102 and 106 shown in FIG. 5) may be defined on the center axis 360. Although not shown in FIG. 18, a window (e.g., window 106 shown in FIGS. 5 and 17) may be positioned between the sample tube 342 and the detector 362.

The cavity 312a may be bounded by a wall 316a of the optical test platform. In some embodiments, two or more alignment ribs 352, 353 may be disposed on the wall 316a of the cavity 312a to help position the sample tube 342 along the center axis 360. In some embodiments, the ribs 352, 353 may be molded as part of the shell 310. In the embodiment depicted in FIG. 18, the alignment ribs 352, 353 may hold the sample tube 342 in a predetermined position (e.g., the position shown in FIGS. 17 and 18) when the legs 348, 349 apply a force in any direction having a force component towards the detector 362. In this manner, the alignment ribs 352, 353 may provide a stable, repeatable position for the sample tube 342 without requiring a precise force vector from the legs 348, 349, and the ribs 352, 353 may guide the sample tube 342 into position, for example, to a position centered along the center axis 360. In some embodiments, the legs 348, 349 may be configured to apply a force to the sample tube 342 towards a point between the legs (e.g., an intersection point of the force vectors 364, 366), with the coiled wire 344 attempting to move the legs 348, 349 in counter-rotating directions about the axis of the helical spring.

The predetermined position of the sample tube 342 may be designed to facilitate a clear, repeatable interrogation of the sample tube using the techniques and apparatus described herein, and the predetermined position may be dependent on the diameter of the sample tube and the spacing between the ribs. In some embodiments, the ribs 352, 353 may be positioned at least at a vertical position of one of the legs 348, 349. In some embodiments, the ribs 352, 353 may be positioned below a vertical position of the legs 348, 349. In some embodiments, the ribs 352, 353 may be positioned between the vertical positions of the legs 348, 349. In some embodiments, the ribs 352, 353 may be positioned at the vertical position of both legs 348, 349. In some embodiments, the legs 348, 349 may disposed on or may apply a force in a horizontal plane, such that the line of action of the spring is on a horizontal plane relative to the optical test platform 300. In some embodiments, the ribs 352, 353 may extend substantially the height of the cavity 312a.

In operation, the sample tube 342 is inserted into the cavity 312a of the optical test platform 310 (shown in FIG. 17). As the sample tube 342 is inserted, the legs 348, 349 are pushed away from the center axis 360 as the rollers 354, 355 allow the sample tube to slide into the cavity 312a. The torque created by the elastic deformation of the coiled wire 344 of the spring 340 may cause each leg 348, 349 to apply a force 364, 366 on the sample tube 342. Each of the forces 364, 366 of the legs 348, 349 may be in a direction that is at least partially towards the center axis 360 and at least partially towards the detector 362.

In some embodiments, the components of the forces 364, 366 that are perpendicular to the center axis 360 may cancel, leaving a net force on the sample tube 342 along the center axis 360 towards the detector 362. The spring 340 may apply a reaction force on the post 346 at a point closest to the detector 362 on the center axis 360. In some embodiments, as described below, the legs 348, 349 may be vertically offset such that there is a slight torque applied to the sample tube 342, and this torque may be counteracted by the structure of the optical test platform (e.g., the ribs 352, 353 and/or guide surface 368). The sample tube 342 may be held vertically within the cavity 312a between the various contact points described herein.

With reference back to FIG. 4, in some embodiments, the spring 340 (shown in FIGS. 17-19) and alignment structures 352, 353, 368 may be configured to position the sample tube 342 (shown in FIGS. 17-18) adjacent the third window 106 such that the density signal 154 is incident upon the sample tube 342 and window 106 perpendicular to their respective surfaces. In such embodiments, the spring 340 may be positioned opposite the window 106 as shown in FIG. 17. In such embodiments, the emitted light 150 may also be incident upon the sample tube perpendicular to its surface, and the emitted light 150 and density signal 154 may travel at least partially along the center axis 360 shown in FIG. 18 (e.g., the detector 362 may receive the density signal 154). In some embodiments, the spring 340 may position the sample tube 342 closer to the third window 106 than to the first window 102 or second window 104, such that in some embodiments the surface of the sample tube may not align with the second window 104 to transmit the nephelometric signal 152 perpendicularly through both surfaces. As detailed herein, in some embodiments, the spring 340 may be configured to position the sample tube adjacent any of the first, second, or third windows, with the alignment ribs on either side of any of the aforementioned windows and the spring opposite any of the aforementioned windows.

When no sample tube 342 is inserted in the cavity 312a, the legs 348, 349 of the spring 340 may engage respective stops 350, 351 on the optical test instrument 310 (shown in FIG. 17). In some embodiments, the stops 350, 351 may be positioned equidistant from the center axis 360 such that the legs 348, 349 remain centered relative to the axis 360 to receive the sample tube 342 therebetween. In some embodiments, the stops 350, 351 may be configured to engage the legs 348, 349 such that the spring 340 is always elastically deformed when positioned on the post 346. In such embodiments, spring 340 may apply a force to the stops 350, 351 when not otherwise obstructed or resisted by the sample tube 342, and the continuous deformation may help create a smooth motion in the spring 340 without slop or slack in the motion or application of force. In some embodiments, the legs 348, 349 may be disposed perpendicular to each other when the legs are engaged with the respective stops 350, 351. In some embodiments, the stops 350, 351 may be positioned such that the legs 348, 349 and rollers 354, 355 protrude vertically over the cavity 312a when no sample tube 342 is inserted. In some embodiments, the stops 350, 351 may be positioned such that the legs 348, 349 and rollers 354, 355 protrude less than half way over the cavity 312a when no sample tube 342 is inserted. In some embodiments, the spring 340 may be positioned between the shell 310 of the optical test platform and the outer housing of the instrument (shown in FIG. 1).

In some embodiments, the stops 350, 351 may be positioned such that, when a sample tube 342 is inserted into the cavity and is held against the ribs 352, 353, the legs 348, 349 comes into contact with the stops. In some embodiments, the sample tube 342 may prevent the legs 348, 349 from contacting the stops 350, 351 when in the predetermined position. In some embodiments, the legs 348, 349 may apply a force (e.g., forces 364, 366) to the sample tube 342 both before and while the sample tube is in the predetermined position against the ribs 352, 353.

Turning to FIG. 19, a perspective view of an embodiment of the spring 340 is shown. In the depicted embodiment, the legs 348, 349 cross each other near the coiled portion of the wire 344. As shown in FIG. 18, the cross over may occur along the center axis 360. Outward force on the legs 348, 349 away from the center axis 360 may cause the coiled wire 344 to torsionally tighten and compress in the depicted embodiment.

Turning back to FIG. 19, the legs 348, 349 may be vertically separated from each other due to the thickness of the spring 340 in the axis of the helical coil, which may cause one leg (e.g., the uppermost leg 349) to protrude over the cavity (e.g., cavity 312a shown in FIGS. 17-18) at a higher position than another leg (e.g., lowermost leg 348). In such embodiments, a torque may be applied to the sample tube 342 in a direction within the horizontal plane (e.g., the plane of the paper in FIGS. 17-18) attempting to move the sample tube out of vertical alignment, and the torque may be counteracted by the structures and guiding surfaces of the optical test platform described herein. In some embodiments, the legs may be bent or otherwise reoriented in another direction while still being able to apply force to the sample tube.

With reference to FIG. 17, in some embodiments, the lower end of the cavity 312a, proximate the lower window 108, may define a U-shaped guide surface 368 oriented with a curved portion 369 defining a semi-circle and a pair of straight portions 370 extending to either side of a window 106. In the depicted embodiment, the curved portion 369 of the guide surface 368 is disposed on the same side of the cavity 312a as the post 346 and majority of the spring 340 such that the force (e.g., forces 364, 366 shown in FIG. 18) of the spring 340 pushes the sample tube 342 along the U-shaped guide surface 368 towards the alignment ribs (e.g., alignment ribs 352, 353 shown in FIG. 18). The U-shaped guide surface 368 may be disposed above the lower window 108, which window may function and be structures according to the embodiments described herein.

The sample tube 342 may engage the guide surface 368 and hold the sample tube upright and vertical against the alignment ribs (e.g., alignment ribs 352, 353 shown in FIG. 18). In some embodiments, the sample tube 342 may have a curved, hemispherical bottom which may rest against a complementarily angled surface of the guide surface 348. The curved portion of the guide surface 368 may define a center of curvature that is offset from the center of the lower window 108 and the center of the cavity 312a, such that the sample tube is positioned closer to a window 106 opposite the spring 340 and post 346 than to the windows 102, 104 on the other surfaces of the wall 316a of the cavity. The guide surface 368 and alignment ribs 352, 353 may cooperate to hold the sample tube 342 substantially vertically within the cavity 312a and may cooperate to hold the sample tube parallel to the wall 316a of the cavity. The curved portion 369 and straight portions 370 may provide a counteracting force to the torque of the offset legs 348, 349 on the embodiment of the spring 340 and sample tube 342 described above.

Turning to FIGS. 20-28 another embodiment of the optical test platform 800 is shown. The optical test platform 800 may include a shell 810 with one or more mounts 820, 822, 824; an aperture 830; upper apertures 814a, 814b; and cavities 812a, 812b that may each be structured and operate in substantially the same manner as the example optical test platforms 100, 300 detailed above. Moreover, embodiments of the optical test platform 800, or portions thereof, may be incorporated into or substituted for portions of the optical test platforms 100, 300 detailed herein. In some embodiments, a first cavity 812a may be used for testing and/or operating on the fluid in a sample tube, while the second cavity 812b includes no testing windows or detectors.

With continued reference to FIG. 17, the optical test platform 800 may include at least one spring 840 that urges a sample tube 842 to a predetermined position within one or more of the cavities 812a, 812b. The spring 840 may include rollers 854, 855 that operate in substantially the same manner as the rollers 354, 355 detailed above. In the embodiment depicted in FIG. 17, the optical test platform 800 includes a spring 840 configured to bias a sample tube 842 towards a window 806. The depicted spring 840 includes a coiled wire 844 disposed around a post 846 (shown in FIG. 21) and two legs 848, 849 defining the respective ends of the wire. The spring 840 may operate as a helical torsion spring, such that the helical coiled wire 844 is twisted about the axis of the coil (e.g., an axis extending perpendicular to the page of FIG. 17) by bending moments applied at the legs 848, 849.

With reference to FIG. 21, an example underside of a portion 11 of the housing of the handheld unit of an optical test instrument (e.g., handheld unit 10 of optical test instrument 1 shown in FIG. 1) is depicted. In the depicted embodiment, the portion 11 of the housing has a post 846 and a pair of stops 849, 850 extending downwardly therefrom towards the optical test platform (e.g., optical test platform 800 shown in FIG. 20). The post 846 and stops 849, 850 may each be structured and operate in substantially the same manner as the post 346 and stops 349, 350 detailed above, except that some or all of the post and stops may be attached to the portion 11 of the housing of the handheld unit instead of the optical test platform. The post and stops may be interchanged, such that a post 846 may be attached to the portion 11 of the housing, while one or more of the stops 349, 350 are attached to the optical test platform, or vice versa.

Turning to FIGS. 22 and 23, in some embodiments, the cavities 812a, 812b of the optical test platform 800 may be at least partially defined by a wall 816a, 816b of the shell 810. In some embodiments, a wall (e.g., wall 816a) may include one or more alignment ribs (e.g., alignment ribs 352, 353 shown in FIG. 18). With continued reference to FIGS. 22 and 23, in some embodiments, the wall 816a may be taller in certain positions than in others. For example, the wall 816a shown in FIGS. 22 and 23 is taller in an area adjacent to the third window 806 and third mount 824 than in an area adjacent to the first window 802 and first mount 820. With reference to FIG. 22, the wall 816a may define a first, taller height from the slot 880 (configured to receive a switch therein for detecting the sample tubes, such as by a mechanical switch) to second window 804, including the third window 806; and the wall 816a may define a second, shorter height from the second window 804 back around to the slot 880, including the first window 802.

In some embodiments, the portion of the wall 816a against which the sample tube (e.g., sample tube 342 shown in FIG. 18) is forced is taller than the portion of the wall adjacent the spring (e.g., spring 340 shown in FIG. 18 and/or spring 840 shown in FIG. 20).

The ribs (e.g., alignment ribs 352, 353 shown in FIG. 18) may be positioned on the first, taller portion of the wall and the spring 840 may be positioned above the second, shorter portion of the wall (e.g., as shown in FIG. 20). In such embodiments, the spring 840 may be positioned in line with the ribs on a generally horizontal plane relative to the optical test platform 800, such that the line of action of the spring is directed at the alignment ribs.

With reference to FIGS. 20 and 22-24, the shell 810 may include guide surfaces 868 having a curved portion 869 and straight portions 870 configured to align and hold the sample tubes (e.g., sample tube 342 shown in FIG. 17) within the cavities 812a, 812b. In the depicted embodiment, the guide surfaces 868 are positioned in both cavities 812a, 812b and are each shaped as U-channels. The depicted guide surface 868 in the cavity 812a with windows 802, 804, 806, 808 is oriented towards the third window 806 such that the guide surface 868 cooperates with the spring 840 and alignment ribs to hold the sample tube vertically in a repeatable, consistent position as described above. The guide surface 868 may taper downwardly and inwardly from a plane or axis on the wall 816a of the cavity 812a towards the window 808, such that the base of the sample tube is guided towards the repeatable, consistent predetermined position as it is inserted.

In some embodiments, the lower window 808 may define a complementary shape to the lower portion of the cavity 812a. With reference to FIGS. 22-24 and 27-28, the lower window 808 may be substantially "U" or "bell" shaped to match the shape of the wall 816a and guide surfaces 868 of the cavity 812a. The lower window 808 may include a raised edge 809 configured to engage the wall 816a. With reference to FIG. 23, the lower window 808 may be enclosed by and firmly fixed to the shell 810 (e.g., by overmolding) at the bottom of the cavity 812a. With reference to FIG. 24, in some embodiments, a lower aperture 830 through which the illumination light is transmitted may be substantially circular (e.g., similar to the aperture 130 described herein). The lower aperture 830 may define a radial center at substantially the horizontal center of the cavity 812a.

With reference to FIGS. 22-24 and 26, in some embodiments, the upper windows 802, 804, 806 may be substantially square and may not extend the full height of the cavity 812a or the channels in which they are seated. The windows 802, 804, 806 may be engaged with the shell 810 according to any of the embodiments disclosed herein. In some embodiments, at least a portion of the windows 802, 804, 806 may be shorter than the second, shorter height of the wall 816a discussed above, such that the spring 840 may operate over the windows. The upper windows 802, 804, 806 may be embedded in the shell 810 (e.g., via overmolding), slid into the shell (e.g., vertically downward into predefined channels), or attached via any other means.

Many modifications and other embodiments of the inventions set forth herein will come to mind to one skilled in the art to which these embodiments of the invention pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Although specific terms are employed herein, they are used in a generic and descriptive sense only and not for purposes of limitation. Unless otherwise noted, the components and functionality of various embodiments of the optical test platform, including the first and second embodiments, may be substantively interchangeable, and unless otherwise noted, the features of one embodiment are the same as each other embodiment. Any individual feature or functionality and any assembly of components may be substituted between the embodiments disclosed herein without departing from the scope of this disclosure. For example, the spring 340; rollers 354, 355; post 346; alignment ribs 352, 353; and/or stops 350, 351 shown in one or more of FIGS. 17-19 may individually, collectively, or partially collectively be incorporated into the embodiments of FIGS. 1-16 or FIGS. 20-28. As another non-limiting example, the guide surfaces 868; the spring 840; the post 846; one or more of the stops 849, 850; the upper windows 802, 804, 806; the wall 816a; and/or the lower window 808 may individually, collectively, or partially collectively be incorporated into the embodiments of FIGS. 1-19.

The invention claimed is:

1. A test platform for facilitating the optical interrogation of a test sample, the test platform comprising:
a shell defining:
a cavity for receiving a sample tube;
a first aperture; and
a second aperture,
wherein the first aperture and the second aperture are each configured to optically couple the cavity with an exterior of the shell;
a first window embedded in the shell across the first aperture; and
a second window embedded in the shell across the second aperture,
wherein the first window and second window are each configured to permit the optical coupling of the cavity with the exterior of the shell,
wherein the first window and the second window are optically coupled via the cavity, and wherein the shell is configured to prohibit optical coupling between the first window and the second window through the shell.

2. The test platform of claim 1, wherein the shell is opaque.

3. The test platform of claim 2, wherein the shell is black.

4. The test platform of claim 1, further comprising a first mount for a first optical component and a second mount for a second optical component, wherein the first mount is optically coupled with the first aperture at the exterior of the shell, wherein the second mount is optically coupled with the second aperture at the exterior of the shell, wherein the first mount is configured to position the first optical component to emit light into the cavity through the first window along a first axis, wherein the second mount is configured to position the second optical component to receive light from the cavity through the second window along a second axis, and wherein the first axis and the second axis are collinear.

5. The test platform of claim 1, further comprising a first mount for a first optical component and a second mount for a second optical component, wherein the first mount is optically coupled with the first aperture at the exterior of the shell, wherein the second mount is optically coupled with the second aperture at the exterior of the shell, wherein the first mount is configured to position the first optical component to emit light into the cavity through the first window along a first axis, wherein the second mount is configured to position the second optical component to receive light from the cavity through the second window along a second axis, and wherein the first axis and the second axis are not collinear.

6. The test platform of claim 1, wherein the shell further comprises a third aperture, and wherein the test platform further comprises:
a third window embedded in the shell,
wherein the third aperture is configured to optically couple the cavity with the exterior of the shell,
wherein the third window is disposed across the third aperture,
wherein the first window, the second window, and the third window are optically coupled via the cavity,
wherein the shell is configured to prohibit optical coupling between the first window, the second window, and the third window through the shell, and
wherein the third window is offset from the first window and the second window, such that the third window is configured to receive a portion of light emitted through the first window along an axis between the first window and the second window that is reflected within the cavity.

7. The test platform of claim 6, wherein the first window and the second window are each arranged on an axis that intersects a central axis of the cavity.

8. The test platform of claim 7, wherein the third window is arranged on a second axis that is perpendicular to the axis of the first and second windows.

9. The test platform of claim 1, wherein at least one of the first window and the second window are molded into the shell of the test platform.

10. The test platform of claim 1, further comprising a first mount positioned adjacent the first aperture on an exterior of the shell, wherein the first mount is configured to receive a first optical component.

11. The test platform of claim 10, wherein the first mount comprises a first bore optically coupled with the first aperture and at least one attachment point, and wherein the first mount is configured to allow the first optical component to attach to the attachment point and optically communicate with the cavity via the first bore and the first aperture.

12. The test platform of claim 11, wherein the first bore, the first aperture, and a first surface of the first window are oriented coaxially along an axis extending through a central axis of the cavity, and wherein the first mount is configured to aim the first optical component towards the central axis along the axis.

13. The test platform of claim 10, further comprising a second mount positioned adjacent the second aperture on an exterior of the shell, wherein the second mount is configured to receive a second optical component.

14. The test platform of claim 13, wherein the first mount is configured to receive an emitter, and wherein the second mount is configured to receive a sensor.

15. The test platform of claim 1, wherein the shell further defines a second cavity configured to receive a second sample tube.

16. The test platform of claim 1, wherein the first window is configured to seal the first aperture, and wherein the second window is configured to seal the second aperture.

17. The test platform of claim 1, further comprising a spring defining a first leg and a second leg, wherein the first leg and the second leg are configured to apply a force on a sample tube towards a point between the first leg and the second leg.

18. The test platform of claim 1, wherein the shell further defines a sample tube aperture that openly connects the cavity to the exterior of the shell, such that the sample tube aperture is configured to removably receive the sample tube therethrough to removably position at least a portion of the sample tube between the first window and the second window.

19. The test platform of claim 18, wherein the shell is sealed at a position opposite the sample tube aperture relative to the cavity.

20. The test platform of claim 19, wherein the shell comprises a third aperture and a third window at the position opposite the sample tube aperture relative to the cavity.

21. The test platform of claim 20, wherein for a first axis, second axis, and third axis, each of which is perpendicular to the other two axes and each of which intersects at a point within the cavity, the first aperture and the second aperture are disposed on the first axis, the sample tube aperture and the third aperture are disposed on the second axis, and a fourth aperture and fourth window are disposed on the third axis; and wherein the shell is opaque at a position on the third axis opposite the fourth aperture.

22. A method of manufacturing a test platform, test platform comprising a shell defining a cavity for receiving a sample tube, a first aperture, and a second aperture, wherein the first aperture and the second aperture are each configured to optically couple the cavity with an exterior of the shell; the test platform further comprising a first window embedded in the shell across the first aperture; and a second window embedded in the shell across the second aperture, wherein the first window and second window are each configured to permit the optical coupling of the cavity with the exterior of the shell, wherein the first window and the second window are optically coupled via the cavity, and wherein the shell is configured to prohibit optical coupling between the first window and the second window through the shell: the method comprising:
embedding the first window and the second window in the shell.

23. The method of claim 22, wherein embedding the first window and the second window in the shell comprises:

positioning the first window and the second window in a shell mold; and molding the shell around the first window and the second window, such that the first window and the second window are embedded in the shell.

24. The method of claim 23, wherein molding the shell around the first window and the second window comprises molding an opaque material around the first window and the second window.

25. The method of claim 22, wherein molding the shell around the first window and the second window comprises permanently affixing the first window and the second window to the shell without adhesives or fasteners.

26. The method of claim 22, wherein molding the shell further comprises molding a first mount for a first optical component and a second mount for a second optical component, wherein the first mount is optically coupled with the first aperture at the exterior of the shell, wherein the second mount is optically coupled with the second aperture at the exterior of the shell, wherein the first mount is configured to position the first optical component to emit light into the cavity through the first window along a first axis, wherein the second mount is configured to position the second optical component to receive light from the cavity through the second window along a second axis, and wherein the first axis and the second axis are collinear.

27. The method of claim 22, wherein molding the shell further comprises molding a first mount for a first optical component and a second mount for a second optical component, wherein the first mount is optically coupled with the first aperture at the exterior of the shell, wherein the second mount is optically coupled with the second aperture at the exterior of the shell, wherein the first mount is configured to position the first optical component to emit light into the cavity through the first window along a first axis, wherein the second mount is configured to position the second optical component to receive light from the cavity through the second window along a second axis, and wherein the first axis and the second axis are not collinear.

* * * * *